(12) United States Patent
Myers et al.

(10) Patent No.: US 8,968,402 B2
(45) Date of Patent: Mar. 3, 2015

(54) ACL IMPLANTS, INSTRUMENTS, AND METHODS

(71) Applicants: ArthroCare Corporation, Austin, TX (US); IMDS Corporation, Providence, UT (US)

(72) Inventors: Thomas H Myers, Marietta, GA (US); Douglas M. Lorang, San Jose, CA (US); Chad W. Lewis, Layton, UT (US); Eric Selvik, Austin, TX (US); Christopher Rodriguez, Costa Mesa, CA (US); George W. White, Corona, CA (US); Luis Amador, Jr., Pflugerville, TX (US)

(73) Assignee: ArthroCare Corporation, Austin, TX (US)

( * ) Notice: Subject to any disclaimer, the term of this patent is extended or adjusted under 35 U.S.C. 154(b) by 86 days.

(21) Appl. No.: 13/655,186

(22) Filed: Oct. 18, 2012

(65) Prior Publication Data

US 2013/0096677 A1    Apr. 18, 2013

Related U.S. Application Data

(60) Provisional application No. 61/548,467, filed on Oct. 18, 2011.

(51) Int. Cl.
*A61F 2/08* (2006.01)
*A61B 17/17* (2006.01)

(52) U.S. Cl.
CPC ....... *A61F 2/0811* (2013.01); *A61F 2002/0835* (2013.01); *A61F 2002/0888* (2013.01);
(Continued)

(58) Field of Classification Search
USPC .................................................... 623/13.13
See application file for complete search history.

(56) References Cited

U.S. PATENT DOCUMENTS

| 3,176,316 A | 4/1965 | Bodell |
| 3,832,931 A | 9/1974 | Talan |

(Continued)

FOREIGN PATENT DOCUMENTS

| CA | CA2181179 | 7/1995 |
| EP | 1836996 | 9/2007 |

(Continued)

OTHER PUBLICATIONS

Ramon A. Ruberte Thiele, M.S., Robert Brick Campbell, M.D., Annunziato Amendola, M.D., Jon K. Sekiya, M.D. Biomechanical Comparison of Figure-of-8 Versus Cylindrical Tibial Inlay Constructs for Arthroscopic Posterior Cruciate Ligament Reconstruction. Arthroscopy. The Journal of Arthroscopic and Related Surgery, vol. 26, No. 7 Jul. 2010: pp. 977-983.

(Continued)

*Primary Examiner* — Sameh Boles
(74) *Attorney, Agent, or Firm* — Craig Buschmann; Brinks Gilson & Lione

(57) ABSTRACT

Systems for single tunnel, double bundle anterior cruciate ligament reconstruction include implant constructs and instruments. The implant constructs provide a combination of cortical fixation and bone tunnel aperture fixation. The implant constructs separate a graft into distinct bundles. The instruments are used to prepare shaped bone tunnels to receive the implant constructs and graft bundles. The instruments are also used to exercise and insert the ligament graft constructs. Methods for reconstructing the antero-medial and postero-lateral bundles of the anterior cruciate ligament may rely on a single femoral tunnel, single or double tibial tunnels, and one or more ligament grafts.

25 Claims, 24 Drawing Sheets

(52) U.S. Cl.
CPC ....... *A61F2/0805* (2013.01); *A61F 2002/0852* (2013.01); *A61F 2250/0007* (2013.01); *A61F 2002/0858* (2013.01); *A61B 17/1714* (2013.01)
USPC .................................................. 623/13.13

(56) References Cited

U.S. PATENT DOCUMENTS

| | | |
|---|---|---|
| 4,187,558 A | 2/1980 | Dahlen et al. |
| 4,411,027 A | 10/1983 | Alexander et al. |
| 4,662,886 A | 5/1987 | Moorse et al. |
| 4,738,255 A | 4/1988 | Goble et al. |
| 4,772,286 A | 9/1988 | Goble et al. |
| 4,773,910 A | 9/1988 | Chen et al. |
| 4,792,336 A | 12/1988 | Hlavacek et al. |
| 4,932,972 A | 6/1990 | Dunn et al. |
| 5,004,474 A | 4/1991 | Fronk et al. |
| 5,037,422 A | 8/1991 | Hayhurst et al. |
| 5,100,417 A | 3/1992 | Cerier et al. |
| 5,112,335 A | 5/1992 | Cazenave |
| 5,171,259 A | 12/1992 | Inoue |
| 5,176,682 A | 1/1993 | Chow |
| 5,207,753 A | 5/1993 | Badrinath |
| 5,234,430 A | 8/1993 | Huebner |
| 5,236,445 A | 8/1993 | Hayhurst et al. |
| 5,258,016 A | 11/1993 | DiPoto et al. |
| 5,268,001 A | 12/1993 | Nicholson et al. |
| 5,306,301 A | 4/1994 | Graf |
| 5,370,662 A | 12/1994 | Stone et al. |
| 5,376,101 A | 12/1994 | Green et al. |
| 5,383,905 A | 1/1995 | Golds et al. |
| 5,393,302 A | 2/1995 | Clark et al. |
| RE34,871 E | 3/1995 | McGuire et al. |
| 5,423,819 A | 6/1995 | Small et al. |
| 5,425,766 A | 6/1995 | Bowald |
| 5,458,601 A | 10/1995 | Young, Jr. et al. |
| 5,464,427 A | 11/1995 | Curtis et al. |
| 5,505,735 A | 4/1996 | Li |
| 5,520,693 A | 5/1996 | McGuire et al. |
| 5,545,180 A | 8/1996 | Le et al. |
| 5,562,669 A | 10/1996 | McGuire |
| 5,571,184 A | 11/1996 | DeSatnick |
| 5,575,819 A | 11/1996 | Amix |
| 5,584,835 A | 12/1996 | Greenfield |
| 5,601,557 A | 2/1997 | Hayhurst |
| 5,632,748 A | 5/1997 | Beck, Jr. et al. |
| 5,645,588 A | 7/1997 | Graf |
| 5,681,320 A | 10/1997 | McGuire |
| 5,707,395 A | 1/1998 | Li |
| 5,709,683 A | 1/1998 | Bagby |
| 5,733,307 A | 3/1998 | Dinsdale |
| 5,827,285 A | 10/1998 | Bramlet |
| 5,871,504 A | 2/1999 | Eaton et al. |
| 5,899,938 A | 5/1999 | Sklar et al. |
| 5,918,604 A | 7/1999 | Whelan |
| 5,935,129 A | 8/1999 | McDevitt et al. |
| 5,957,953 A | 9/1999 | DiPoto et al. |
| 5,961,520 A | 10/1999 | Beck, Jr. et al. |
| 5,984,966 A | 11/1999 | Kiema et al. |
| 5,997,539 A | 12/1999 | Errico et al. |
| 6,001,100 A | 12/1999 | Sherman et al. |
| 6,001,106 A | 12/1999 | Ryan et al. |
| 6,022,356 A | 2/2000 | Noyes et al. |
| 6,022,373 A | 2/2000 | Li |
| 6,056,752 A | 5/2000 | Roger |
| 6,099,530 A | 8/2000 | Simonian et al. |
| 6,099,568 A | 8/2000 | Simonian et al. |
| 6,110,207 A | 8/2000 | Eichhorn et al. |
| 6,129,762 A | 10/2000 | Li |
| 6,193,754 B1 | 2/2001 | Seedhom |
| 6,221,107 B1 | 4/2001 | Steiner et al. |
| 6,235,057 B1 | 5/2001 | Roger et al. |
| 6,264,694 B1 | 7/2001 | Weiler |
| 6,283,996 B1 | 9/2001 | Chervitz et al. |
| 6,290,711 B1 | 9/2001 | Caspari et al. |
| 6,355,066 B1 | 3/2002 | Kim |
| 6,379,361 B1 | 4/2002 | Beck, Jr. et al. |
| 6,440,134 B1 | 8/2002 | Zaccherotti et al. |
| 6,497,726 B1 | 12/2002 | Carter et al. |
| 6,508,830 B2 | 1/2003 | Steiner |
| 6,517,542 B1 | 2/2003 | Papay et al. |
| 6,517,578 B2 | 2/2003 | Hein |
| 6,517,579 B1 | 2/2003 | Paulos et al. |
| 6,533,802 B2 | 3/2003 | Bojarski et al. |
| 6,547,564 B1 | 4/2003 | Hansson |
| 6,554,862 B2 | 4/2003 | Hays et al. |
| 6,562,043 B1 | 5/2003 | Chan |
| 6,579,295 B1 | 6/2003 | Supinski |
| 6,599,289 B1 | 7/2003 | Bojarski et al. |
| 6,616,694 B1 | 9/2003 | Hart |
| 6,623,524 B2 | 9/2003 | Schmieding |
| 6,629,977 B1 | 10/2003 | Wolf |
| 6,632,245 B2 | 10/2003 | Kim |
| 6,652,560 B1 | 11/2003 | Gerke et al. |
| 6,652,563 B2 | 11/2003 | Dreyfuss |
| 6,656,183 B2 | 12/2003 | Colleran et al. |
| 6,679,890 B2 | 1/2004 | Margulies et al. |
| 6,712,849 B2 | 3/2004 | Re et al. |
| 6,716,234 B2 | 4/2004 | Grafton |
| 6,723,099 B1 | 4/2004 | Goshert |
| 6,780,187 B2 | 8/2004 | Supinski |
| 6,818,010 B2 | 11/2004 | Eichhorn et al. |
| 6,863,671 B1 | 3/2005 | Strobel et al. |
| 6,878,166 B2 | 4/2005 | Clark et al. |
| 6,887,271 B2 | 5/2005 | Justin et al. |
| 6,893,462 B2 | 5/2005 | Buskirk et al. |
| 6,902,573 B2 | 6/2005 | Strobel et al. |
| 6,902,578 B1 | 6/2005 | Anderson et al. |
| 6,923,810 B1 | 8/2005 | Michelson |
| 6,932,841 B2 | 8/2005 | Sklar et al. |
| 6,942,666 B2 | 9/2005 | Overaker et al. |
| 7,001,390 B2 | 2/2006 | Gebhardt et al. |
| 7,008,451 B2 | 3/2006 | Justin et al. |
| 7,025,786 B2 | 4/2006 | Goble et al. |
| 7,063,724 B2 | 6/2006 | Re et al. |
| 7,137,996 B2 | 11/2006 | Steiner et al. |
| 7,141,066 B2 | 11/2006 | Steiner et al. |
| 7,144,424 B2 | 12/2006 | Steenlage |
| 7,189,251 B2 | 3/2007 | Kay |
| 7,201,773 B2 | 4/2007 | Steiner et al. |
| 7,211,088 B2 | 5/2007 | Grafton et |
| 7,217,279 B2 | 5/2007 | Reese |
| 7,235,074 B1 | 6/2007 | Sklar et al. |
| 7,235,100 B2 | 6/2007 | Martinek |
| 7,261,716 B2 | 8/2007 | Strobel et al. |
| 7,309,356 B2 | 12/2007 | Steiner |
| 7,322,978 B2 | 1/2008 | West, Jr. |
| 7,326,247 B2 | 2/2008 | Morgan |
| 7,329,281 B2 | 2/2008 | Hays et al. |
| 7,335,230 B2 | 2/2008 | Goulet et al. |
| 7,338,531 B2 | 3/2008 | Ellis et al. |
| 7,347,872 B2 | 3/2008 | Goulet et al. |
| 7,468,074 B2 | 12/2008 | Guederian |
| 7,500,983 B1 | 3/2009 | Kaiser et al. |
| 7,530,990 B2 | 5/2009 | Perriello et al. |
| 7,566,339 B2 | 7/2009 | Fallin et al. |
| 7,637,949 B2 | 12/2009 | Hart |
| 7,651,528 B2 | 1/2010 | Montgomery et al. |
| 7,686,838 B2 | 3/2010 | Wolf et al. |
| 7,695,503 B1 | 4/2010 | Kaiser et al. |
| 7,727,278 B2 | 6/2010 | Olsen et al. |
| 7,749,226 B2 | 7/2010 | Stone |
| 7,763,071 B2 | 7/2010 | Bianchi et al. |
| 7,776,039 B2 | 8/2010 | Bernstein et al. |
| 7,776,077 B2 | 8/2010 | Kaiser et al. |
| 7,819,898 B2 | 10/2010 | Stone et al. |
| 7,942,914 B2 | 5/2011 | Cerundolo |
| 7,963,983 B2 | 6/2011 | Cerundolo |
| 7,967,843 B2 | 6/2011 | Kaiser |
| 7,967,861 B2 | 6/2011 | Montgomery et al. |
| RE42,526 E | 7/2011 | Reiser et al. |
| 8,007,533 B2 | 8/2011 | Zhukauskas et al. |
| 8,029,537 B2 | 10/2011 | West, Jr. et al. |
| 8,034,076 B2 | 10/2011 | Criscuolo et al. |
| 8,048,158 B2 | 11/2011 | Hays et al. |

(56) References Cited

U.S. PATENT DOCUMENTS

| | | |
|---|---|---|
| 8,114,094 B2 | 2/2012 | Berberich |
| 8,137,382 B2 | 3/2012 | Denham et al. |
| 8,137,400 B2 | 3/2012 | Shino |
| 8,162,997 B2 | 4/2012 | Struhl |
| 8,192,490 B2 | 6/2012 | Baird et al. |
| 8,226,716 B2 | 7/2012 | Mckernan et al. |
| 8,231,674 B2 | 7/2012 | Albertorio et al. |
| 8,282,647 B2 | 10/2012 | Re |
| 8,298,284 B2 | 10/2012 | Cassani |
| 8,333,802 B2 | 12/2012 | Dougherty |
| 8,343,161 B2 | 1/2013 | Re |
| 8,435,294 B2 | 5/2013 | Montgomery |
| 8,444,652 B2 | 5/2013 | Amis et al. |
| 8,491,595 B2 | 7/2013 | Volpi et al. |
| 8,535,377 B2 | 9/2013 | Myers et al. |
| 8,579,975 B2 | 11/2013 | Myers |
| 8,617,168 B2 | 12/2013 | Bourque et al. |
| 8,617,241 B2 | 12/2013 | Myers |
| 8,647,385 B2 | 2/2014 | Boucher et al. |
| 8,702,796 B2 | 4/2014 | Myers |
| 8,784,426 B2 | 7/2014 | Smith et al. |
| 8,790,352 B2 | 7/2014 | Smith et al. |
| 2002/0007182 A1 | 1/2002 | Kim |
| 2002/0161439 A1 | 10/2002 | Strobel et al. |
| 2002/0165611 A1 | 11/2002 | Enzerink et al. |
| 2003/0009173 A1 | 1/2003 | McGuire et al. |
| 2003/0065390 A1 | 4/2003 | Justin et al. |
| 2003/0130735 A1 | 7/2003 | Rogalski |
| 2003/0171810 A1 | 9/2003 | Steiner |
| 2003/0171811 A1 | 9/2003 | Steiner et al. |
| 2003/0191530 A1 | 10/2003 | Sklar |
| 2003/0216780 A1 | 11/2003 | Fitts et al. |
| 2003/0233095 A1 | 12/2003 | Urbanski et al. |
| 2004/0024456 A1 | 2/2004 | Brown et al. |
| 2004/0030385 A1 | 2/2004 | Steiner |
| 2004/0153153 A1 | 8/2004 | Elson |
| 2004/0172034 A1 | 9/2004 | Re et al. |
| 2004/0199166 A1 | 10/2004 | Schmieding et al. |
| 2004/0243132 A1 | 12/2004 | Whittaker et al. |
| 2004/0267318 A1 | 12/2004 | Boucher et al. |
| 2004/0267361 A1 | 12/2004 | Donnelly et al. |
| 2005/0010289 A1 | 1/2005 | McKernan et al. |
| 2005/0071004 A1 | 3/2005 | Re et al. |
| 2005/0075668 A1 | 4/2005 | Lizardi |
| 2005/0096743 A1 | 5/2005 | Schmieding et al. |
| 2005/0159812 A1 | 7/2005 | Dinger et al. |
| 2005/0171603 A1 | 8/2005 | Justin et al. |
| 2005/0203623 A1 | 9/2005 | Steiner et al. |
| 2006/0030940 A1 | 2/2006 | Schmieding |
| 2006/0052787 A1 | 3/2006 | Re et al. |
| 2006/0095130 A1 | 5/2006 | Caborn et al. |
| 2006/0142769 A1 | 6/2006 | Collette |
| 2006/0155287 A1 | 7/2006 | Montgomery et al. |
| 2006/0155619 A1 | 7/2006 | Shino |
| 2006/0247642 A1 | 11/2006 | Stone et al. |
| 2006/0247790 A1 | 11/2006 | McKay |
| 2006/0265064 A1 | 11/2006 | Re et al. |
| 2007/0156151 A1 | 7/2007 | Guan et al. |
| 2007/0218424 A1 | 9/2007 | Vuorisalo |
| 2007/0225805 A1 | 9/2007 | Schmieding |
| 2007/0239275 A1 | 10/2007 | Willobee |
| 2007/0250067 A1 | 10/2007 | Schmieding et al. |
| 2007/0250166 A1 | 10/2007 | McKay |
| 2007/0270857 A1 | 11/2007 | Lombardo et al. |
| 2008/0097453 A1 | 4/2008 | Stone |
| 2008/0097604 A1 | 4/2008 | Strobel et al. |
| 2008/0119929 A1 | 5/2008 | Schmieding |
| 2008/0147063 A1 | 6/2008 | Cauldwell et al. |
| 2008/0177291 A1 | 7/2008 | Jensen et al. |
| 2008/0188935 A1 | 8/2008 | Saylor et al. |
| 2008/0200992 A1 | 8/2008 | Koob et al. |
| 2008/0234819 A1 | 9/2008 | Schmieding |
| 2008/0269743 A1 | 10/2008 | McNamara et al. |
| 2008/0317812 A1 | 12/2008 | Zhang et al. |
| 2009/0012522 A1 | 1/2009 | Lob |
| 2009/0018654 A1 | 1/2009 | Schmieding et al. |
| 2009/0036927 A1 | 2/2009 | Vestgaarden |
| 2009/0131986 A1 | 5/2009 | Lee et al. |
| 2009/0157119 A1 | 6/2009 | Hale |
| 2009/0171355 A1 | 7/2009 | Amis et al. |
| 2010/0049258 A1 | 2/2010 | Dougherty |
| 2010/0049319 A1 | 2/2010 | Dougherty |
| 2010/0249930 A1 | 9/2010 | Myers |
| 2010/0262184 A1 | 10/2010 | Dreyfuss |
| 2010/0268233 A1 | 10/2010 | Stone |
| 2011/0009885 A1 | 1/2011 | Graf et al. |
| 2011/0137416 A1 | 6/2011 | Myers |
| 2012/0022588 A1 | 1/2012 | Berg |
| 2012/0059469 A1 | 3/2012 | Myers |
| 2012/0109136 A1 | 5/2012 | Bourque et al. |
| 2012/0165868 A1 | 6/2012 | Burkhart et al. |
| 2012/0283830 A1 | 11/2012 | Myers |
| 2012/0283832 A1 | 11/2012 | Boucher et al. |
| 2012/0296427 A1* | 11/2012 | Conner et al. ............. 623/13.13 |
| 2013/0023928 A1 | 1/2013 | Dreyfuss |
| 2013/0030527 A1 | 1/2013 | Ammann |
| 2013/0046353 A1 | 2/2013 | McCarthy et al. |
| 2013/0085503 A1 | 4/2013 | Smith et al. |
| 2013/0085568 A1 | 4/2013 | Smith et al. |
| 2013/0096677 A1 | 4/2013 | Myers et al. |
| 2013/0253524 A1 | 9/2013 | Amis et al. |
| 2013/0261677 A1 | 10/2013 | Bouduban et al. |
| 2013/0331941 A1 | 12/2013 | Myers et al. |
| 2014/0031932 A1 | 1/2014 | Myers |
| 2014/0088606 A1 | 3/2014 | Bourque et al. |

FOREIGN PATENT DOCUMENTS

| | | |
|---|---|---|
| WO | WO9519141 | 7/1995 |
| WO | WO2010120520 | 10/2010 |
| WO | WO2012031007 | 3/2012 |

OTHER PUBLICATIONS

Lenschow, S., et al. Structural Properties of a New Device for Graft Fixation In Cruciate Ligament Reconstruction: The Shim Technique. Arthroscopy Orthopedic Trauma Surg. (2011) 131:1067-1072.

Lenschow, S., et al. Structural Properties of a New Fixation Strategy in Double Bundle ACL Reconstruction: The MiniShim. Arthroscopy Orthopedic Trauma Surg. (2011) 131: 1159-1165.

Basdekis George, Christel Pascal, Anne Francois. Validation of the Position of the Femoral Tunnels in Anatomic Double-Bundle ACL Reconstruction with 3-D CT Scan, Knee Surg Sports Traumatol Arthrosc (2009) 17:1089-1094.

Cha Peter, Brucker Peter, West Robin, Zelle Boris, Yagi Masayoshi, Kurosaka Masahiro, Fu Freddie. Arthroscopic Double-Bundle Anterior Cruciate Ligament Reconstruction: An Anatomic Approach, Techinical Notes: Arthroscopy vol. 21, No. 10, Oct. 2005: pp. 1275-1277.

Duthon VB, Barea C, Abrassart S, Fasel JH, Fritschy D, Menetrey J. Anatomy of the anterior cruciate ligament. Knee Surgery Sports Traumatoloty Arthroscopy 2006;14(3):204-213.

Fu FH, Lo MY, Lo MS, Pombo MW, Singleton R. Anatomic double-bundle ACL reconstruction: patient information handout/frequently asked questions. Department of Orthopedic Surgery, University of Pittsburgh. Not formally published. No date.

Freddie H. Fu, C. Benjamin. Anterior Cruciate Ligament Reconstruction Using Quadruple Hamstring. Operative Techniques in Orthopaedics, vol. 9 No. 4 Oct. 1999: pp. 264-272.

Hara K, Mochizuki T, Sekiya I, Yamaguchi K, Akita K, Muneta T. Anatomy of normal human anterior cruciate ligament attachments evaluated by divided small bundles. The American Journal of Sports Medicine 2009; 37(12) :2386-2391.

Marshall JL, Warren RF, Wickiewicz TL, Reider B. The Anterior Cruciate Ligament: A Technique of Repair and Reconstruction, Clinical Orthopaedics and Related Research No. 143 Sep. 1979 pp. 97-106.

Masaaki Takahashi, Mitsuhito Doi, Masashi Abe, Daisuke Suzuki, Akira Nagano. Anatomical Study of the Femoral and Tibial Inser-

(56) References Cited

OTHER PUBLICATIONS tions of the Anteromedial and Posterolateral Bundles of Human Anterior Cruciate Ligament. Am J Sports Med 2006 34: 787.

Milano Giuseppe, Mulas Pier, Ziranu Fabio, Piras Stefano, Manunta Andrea, Fabbriciani Carlo. Camparison Between Different Femoral Fixation Devices for ACL Reconstruction With Doubled Hamstring Tendon Graft: A Biomechanical Analysis.

Mitsuhito Doi, Masaaki Takahashi, Masashi Abe, Daisuke Suzuki, Akira Nagano. Lateral Radiographic Study of the Tibial Sagital Insertions of the Anteromedial and Posterolateral Bundles of Human Anterior Cruciate Ligament. Knee Surg Sports Traumatol (2009) 17: 347-351.

Mochizuki T, Muneta T, Nagase T, Shirasawa SI, Akita KI, Sekiya I. Cadaveric knee obervation study for describing anatomic femoral tunnel placement for two-bundle anterior cruciate ligament reconstruction. Arthroscopy 2006;22(4):356-361.

Craig D. Morgan, Divid Caborn. Anatomic Graft Fixation Using a Retrograde Biointerference Screw for Endoscopic Anterior Cruciate Ligament. Reconstruction: Single-Bundle and 2-Bundle Techniques. Techniques in Orthopaedis 20(3): 297-302 2005.

Petersen W, Zantop T. Anatomy of the anterior cruciate ligament with regard to its two bundles. Clinical Orthopedics and Related Research 2007;454:35-47.

Ranawat A, Fu FH. Double bundle ACL reconstruction restores anatomy, kinematics. Orthopedics Today 2007;27:94.

Joel T. Rohrbough, Russell F. Warren, Thomas Wickiewicz. Posterior Cruciate Ligament Reconstruction: Single Versus Double-Bundle Technique, Techiniques in Orthopaedics 16(2): 119-126 2001.

Takanori Iriuchishima, Sheila Ingham, Goro Tajima, Takashi Horaguchi, Akiyoshi Saito, Yasuake Tokuhashi, Albert Van Houten, Maarten Aerts, Freddie Fu. Evaluation of the Tunnel Placement in the Anatomical Double-Bundle ACL Reconstruction: a Cadaver Study. Knee Surg Sports Traumatol Arthrosc. DOI 10.1007/s00167-010-1128-y.

Tallay Andras, Lim Mui-Hong, Bartlett John. Anatomical Study of the Human Anterior Cruciate Ligament Stum's Tiial Insertion Footprint. Knee Surg Sports Traumatol Arthrosc (2008) 16:741-746.

Tan JI, Chang PCC, Mitra AK, Tay BK. Anthropometry of Anterior Cruciate Ligament in Singaporean Chinnese. Ann Acad Med Singapore 1998; 27:776-9.

Carola van Eck, Cesar Martins, Shail Vyas, Umberto Celentano, C. Niek van Dijk, Freddie Fu. Femoral intercondylar notch shape and dimensions in ACL injured patients. Knee Surg. Sports Traumatol Arthoroscopic. DOI 10.1007/s00167-010-1135-z.

Wang JQ, Ao YF, Yu CL, Liu P, Xu Y, Chen LX. Clinical evaluation of double-bundle anterior cruciate ligament reconstruction procedure using hamstring tendon grafts: a prospective, randomized and controlled study. Chinese Medical Journal 2009;122(6):706-711.

Yong Seuk Lee, Sung Kon Kim, Jung Ho Park, Jong Woong Park, Joon Ho Wnag, Young Bok Jung, Jin Hwan Ahn. Double-Bundle Anterior Cruciate Ligament Reconstruction Using Two Different Suspensory Femoral Fixation: A Technical Note. Knee Surg Sports Traumatol Arthrosc. (20007) 15:1023-1027.

Zaffagnini Stefano, Bruni Danilo, Martelli Sandra, Imakiire Naoaki, Marcacci Maurilio, Russo Alessandro. Double-bundle ACL reconstruction; Influence of Femoral Tunnel Orientationin Knee Laxity Analysed with a Navigation System—an in vitro Biomechanical Study. *BMC Musculoskeletal Disorders* 2008, 9:25doi:10.1186/1471-2474-9-25 http://www.biomedcentral.com/1471-2474/9/25.

Office Action (Second) for Chinese Patent Application No. 201080024905.2, dated Aug. 4, 2014 (10 pages).

Search Report for Chinese Patent Application No. 201080024905.2, dated Jul. 25, 2014 (2 pages).

\* cited by examiner

ACL IMPLANTS, INSTRUMENTS, AND METHODS

CROSS-REFERENCE TO RELATED APPLICATIONS

This application claims the benefit of:

U.S. Provisional Patent Application No. 61/548,467, filed Oct. 18, 2011, and is entitled: ACL IMPLANTS, INSTRUMENTS, AND METHODS.

The above-identified document is hereby incorporated by reference in its entirety.

BACKGROUND

The present disclosure relates to anterior cruciate ligament (ACL) repair surgery. More precisely, the present invention relates to implants, systems, methods of use and instruments for double bundle ACL repair, including securing an ACL graft with a cortical fixation device and separating the graft into multiple bundles with an aperture fixation device so as to approximate the natural bundles of an intact ACL. For example, the systems, apparatus, and methods disclosed herein may be applicable to tibial or femoral fixation of a doubled hamstring tendon graft. It is contemplated that the systems and methods set forth herein, or adaptations, may be useful in suspensory fixation applications beyond anterior cruciate ligament repair.

It is generally accepted in the field of orthopedic surgery that the anterior cruciate ligament does not heal itself after injury. Initial attempts at repair of this ligament resulted in nearly uniform failure of the ligament to stabilize the knee joint.

Over the course of the last four decades, practitioners have turned to methods of ligament reconstruction in attempts to restore knee stability and normal knee kinematics. Most surgeons have become proficient with a ligament reconstruction technique involving autograft or allograft replacement of the native ACL. Autografts, which are harvested from the patient's own body, may comprise bone-patellar tendon-bone (BPTB), hamstring tendon (HT), or occasionally quadriceps tendon (QT). Allografts, which are harvested from a donor, may comprise patellar tendon, quadriceps tendon, Achilles tendon, tibialis anterior tendon, hamstring tendons, or occasionally peroneal tendons. Any of these grafts may be placed so that it traverses the intercondylar notch and its ends rest within tibial and femoral bone tunnels.

Two important surgical factors in achieving a stable, fully functional, pain-free knee after ACL reconstruction are correct placement of the femoral and tibial tunnels, so that the ACL graft does not impinge the posterior cruciate ligament (PCL) or the roof of the intercondylar notch, and the use of slip-resistant, stiff, strong fixation for the ends of the graft.

Tibial and femoral bone tunnel placement has been a very controversial topic. Anterior placement of the femoral tunnel has become generally accepted as a technical cause of graft failure. Recently, after years of transtibial placement of the femoral bone tunnel, it has become increasingly popular to drill the femoral tunnel separately (i.e., through a medial arthroscopic portal). This may result in more anatomic placement of the femoral tunnel and improved graft orientation.

There are currently many options for graft fixation. Many surgeons who prefer BPTB grafts use interference screw fixation. However, among surgeons who prefer soft tissue grafts, a wide variety of fixation devices are used with little consensus as to what is best. Soft tissue graft fixation can be broadly divided into interference screw-based fixation, cortical fixation, and cross pin fixation.

Interference screw-based fixation of soft tissue grafts may be used in the femur and tibia. This type of fixation generates friction between the graft and the bone tunnel. Many surgeons who were originally trained in BPTB grafts continue to use this method of fixation when they use soft tissue grafts. Metal and bioabsorbable interference screws are currently available. However, there are no interference screws that have demonstrated bony ingrowth, which would be beneficial over the long term.

Cortical fixation may be preferred by surgeons who primarily use soft tissue grafts. A number of devices are known to take advantage of the innate strength of cortical bone. As early as 1966, German surgeon Helmut Bruckner described an ACL reconstruction technique in which a BPTB graft was secured by sutures to a button resting on the lateral aspect of the lateral femoral condyle. Other examples of cortical fixation devices include Endobutton™ (Smith and Nephew) and EZLoc™ (Biomet). Cortical fixation devices have been shown to have some of the highest pullout strengths of any soft tissue graft fixation device. In the femur, these devices may comprise an extracortical anchor attached to a fabric or suture loop. Such a device may be used by draping the graft over the fabric loop, supporting the anchor against the exterior cortical surface so that the graft is suspended within the tunnel, and securing the fabric loop to the anchor. In the tibia, cortical fixation may be achieved by stitching sutures to the free ends of the graft, placing a screw through the anterior tibial cortex, tying the sutures around the screw, and compressing the sutures against the cortex with a washer.

Cross-pin fixation has been gaining in popularity, at least in part because of the perception that it may provide secure fixation closer to the tunnel aperture than that provided by cortical fixation. Cross-pin fixation may be achieved by passing a pin across a bone tunnel close to the aperture and draping the graft over the pin where it crosses the tunnel.

Although there may be little evidence that aperture fixation provides greater stability than does cortical fixation, many surgeons prefer aperture fixation because it may avoid the so-called "bungee effect" of cortical fixation devices. This theory presumes that an ACL reconstruction spanning a longer distance between fixation points will have greater elasticity than an ACL reconstruction spanning a shorter distance. Fixation closer to the joint space may provide higher stability than remote fixation at the cortex because the distance across the joint space is much less than the distance between extracortical fixation points. However, a 2005 meta-analysis of stability after ACL reconstruction showed cortical fixation to be associated with the highest rates of ACL reconstruction stability for soft tissue grafts.

There may be biomechanical evidence that aperture fixation may lead to increased graft stiffness. On the tibia, distal cortical fixation of a soft tissue ACL graft may be stronger, stiffer, and more slip resistant than is aperture fixation with an interference screw alone. The use of an interference screw alone may cause tunnel widening and may prevent circumferential tendon-tunnel healing, which may result in inferior strength and stiffness at 4 weeks compared with cortical fixation. However, the insertion of a bone dowel alongside a tendon graft in the tunnel, in conjunction with distal cortical fixation, may prevent tunnel widening, increase stiffness, promote circumferential healing, and simplify revision surgery.

Aggressive, brace-free rehabilitation with early weight bearing may be safe following high-stiffness, slip-resistant fixation. The high stiffness provided by distal cortical fixation may reduce the graft tension required to restore stability and may lower graft tension during open-chain exercise. Reducing the graft tension without increasing anterior laxity requires high-stiffness fixation which also resists slipping and tension loss during aggressive rehabilitation. Whipstitch-post tibial cortical fixation was the first fixation method used successfully for quadrupled hamstring grafts. Simple interference screw fixation has had mixed results, while interference screw fixation combined with cortical fixation has shown very good results. Similarly, interference screw-based methods such as the Intrafix™ (DePuy Mitek) appear to be promising constructs on the tibial side. Although cross-pin fixation on the tibial side may be popular among surgeons, there is a paucity of clinical data pertaining to it, and the clinical series that have been published to date have shown mixed results.

Despite advancements in single bundle ACL reconstruction, a review of the literature demonstrates that between 10% and 30% of patients report persistent instability following single bundle ACL reconstruction surgery. Among single bundle ACL reconstructions, only 70% of KT1000 test results demonstrate a <2 mm side-to-side difference, with a failure rate of 5% to 10%. The return-to-sport rate for single bundle restorations is only 60% to 70%.

Anatomic studies reveal that the ACL has two functional bundles: the anteromedial (AM) bundle and the posterolateral (PL) bundle. The bundles are named according to their tibial insertion sites. With the knee in extension, the AM and PL bundles are parallel to each other and are oriented generally along the mechanical axis of the leg. When the knee is flexed to 90 degrees, the AM and PL bundles are crossed. This occurs because the PL bundle femoral insertion site is posterior to the AM bundle femoral insertion site when the knee is in extension, and anterior to the AM bundle femoral insertion site when the knee is flexed to 90 degrees. In other words, the AM bundle femoral insertion site rotates over the PL bundle femoral insertion site as the knee flexes. As a result, each bundle makes a unique contribution to knee kinematics at different knee flexion angles. In extension, the PL bundle tightens and the AM bundle relaxes, whereas in flexion, the AM bundle tightens as the μL bundle becomes lax. The AM bundle is the primary restraint against anterior tibial translation and the PL bundle tends to stabilize the knee in full extension, particularly against rotational loads.

Anatomic double bundle ACL reconstruction has some logical rationales in its favor and is supported by biomechanical studies. These studies suggest that conventional single bundle ACL reconstruction may successfully restore anteroposterior knee stability, but the reconstructed knee may be unable to resist combined rotatory loads. Cadaveric studies of double bundle knee reconstructions reveal a closer restoration of normal knee kinematics and better rotational stability. A closer restoration of normal knee kinematics may be associated with improved functional outcomes following ACL reconstruction.

Reciprocal tensile behavior has long been a quest of the surgeon who performs ACL reconstructions and has been a rationale for pursuing the double bundle technique. The concept is that the AM bundle should carry more tension in flexion and the PL bundle should carry more tension in extension. A doubled-over soft tissue graft in a single tunnel may restore reciprocal tensile behavior if the tunnel has been placed to avoid PCL and roof impingement and the centers of the graft bundles can be separated and appropriately oriented at the femoral and tibial tunnel apertures.

Double bundle ACL reconstruction is not without its challenges. The most common cause of failure of any kind of ACL reconstruction is improper bone tunnel position. The double bundle procedure, which is more complex than the single bundle technique, has more risk of misplaced bone tunnels. For example, dual tunnels can interfere with each other when they are not meticulously positioned. In particular, a poorly positioned PL tunnel may displace a subsequently formed AM tunnel too far anteriorly, resulting in roof impingement and potential graft rupture.

The double bundle procedure has other potential challenges. The greater complexity of double bundle repair may result in longer surgical time. Two separate grafts need to be prepared, four tunnels need to be prepared, and four separate fixation devices are required.

Suitable femoral fixation options may be limited. Currently, the EndoButton™ may be the most common femoral fixation device for a double bundle ACL reconstruction due to its low profile. Cross-pin femoral fixation may not be feasible for double bundle ACL reconstruction due to anatomical constraints in the vicinity of the femoral tunnel apertures.

A larger tibial footprint of a double bundle ACL reconstruction may offer greater potential for femoral notch impingement by the graft. Larger cross-sectional areas of graft tissue can traverse the intercondylar notch in a double bundle ACL reconstruction. This may result in PCL impingement as well as notch impingement due to the size of the grafts. PCL impingement has been seen even in single bundle ACL reconstructions. PCL impingement may occur when the tibial tunnel is placed in a vertical orientation at an angle >70 degrees from the medial joint line of the tibia and the femoral tunnel is then drilled through the tibial tunnel. Vertical placement of the ACL graft at the apex of the femoral notch may cause the graft to wrap around the PCL, which may cause high tension in the graft when the knee is flexed. High graft tension in flexion may cause the graft to stretch out or may prevent the patient from regaining full knee flexion. Preventing PCL impingement in single bundle ACL reconstructions requires a femoral notchplasty as well as placement of the femoral tunnel further down the sidewall of the intercondylar notch. PCL impingement may not be an issue with double bundle reconstructions, because the femoral tunnels may be placed in the anatomic footprint of the ACL through an inferomedial arthroscopic portal. However, when two femoral tunnels are separated by a bone bridge (often 2 mm wide), the composite area may extend outside the border of the anatomic ACL footprint. This effectively increases the cross-sectional area of the graft and "overstuffs the notch." Furthermore, the cross-sectional area of the native ACL as it crosses the PCL is approximately 54.4 square mm, and may be significantly less in smaller people. Therefore, if double bundle ACL reconstruction with a standard size graft is performed with dual femoral and tibial tunnels, the effective cross-sectional area of the graft may exceed 100 square mm. Notch or PCL impingement, loss of knee flexion and eventual stretching and failure of the tissue may result.

Revision is also more difficult with double bundle ACL reconstruction than with single bundle ACL reconstruction. A significant volume of bone is consumed with a four tunnel technique. It may be problematic to place revision tunnels anatomically if there is no bone into which to drill. In order to ensure correct graft placement at the time of revision, a bone grafting procedure may be required to fill the vacant bone tunnels, followed by a second procedure to revise the ACL reconstruction.

Thus, there exists a need in the art for novel ACL reconstruction devices that provide the strength of cortical fixation, the stiffness of aperture fixation, and osteoconductivity for bony ingrowth to allow circumferential healing of the graft/ tunnel interface. There also exists a need for a method of fixation that separates an ACL graft into bundles such that knee kinematics are restored without the need for separate bone tunnels and multiple soft tissue grafts. There also exists a need in the art for an ACL reconstruction technique that produces bone tunnels that more closely replicate the anatomic femoral and tibial ACL footprints, uses a single graft separated into bundles to restore the kinematics of the native ACL, and eliminates the problems of increased surgical time and complexity, difficult revision, notch impingement and PCL impingement that are inherent with the current double tunnel, double bundle ACL technique. There also exists a need in the art to provide a fixation implant that can be used to deliver specific therapeutic agents, such as biochemicals that allow for tendon to bone healing or enhance osteoinductivity such that bone may grow into the fixation implant.

BRIEF DESCRIPTION OF THE DRAWINGS

Various embodiments of the present disclosure will now be discussed with reference to the appended drawings. It will be appreciated that these drawings depict only typical examples of the present disclosure and are therefore not to be considered limiting of the scope of the invention.

DETAILED DESCRIPTION

Figure 1:
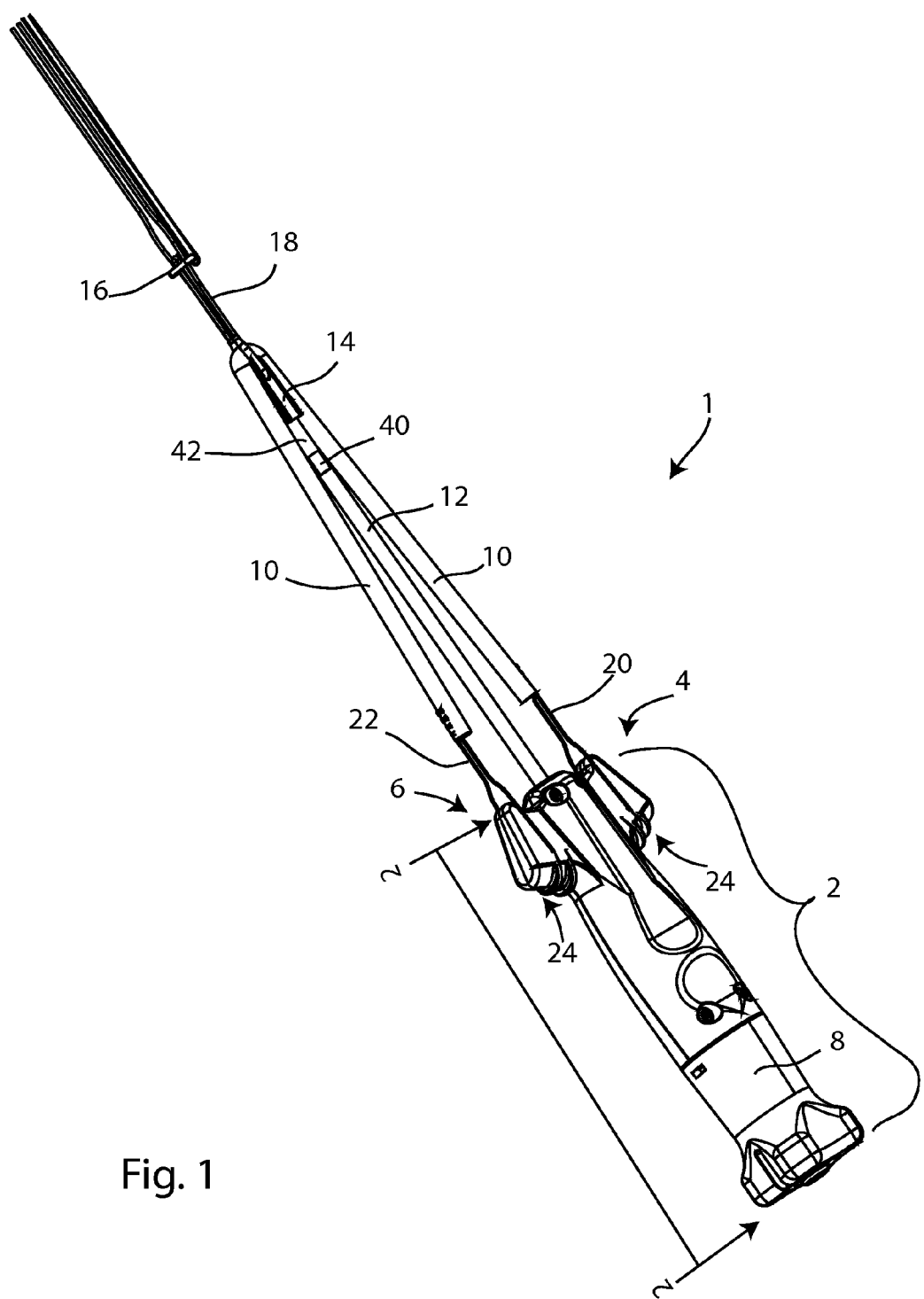
FIG. 1 is a perspective view of a surgical tool 1 for inserting a tensioned ligament into a patient.

In this specification, standard medical directional terms are employed with their ordinary and customary meanings. Superior means toward the head. Inferior means away from the head. Anterior means toward the front. Posterior means toward the back. Medial means toward the midline, or plane of bilateral symmetry, of the body. Lateral means away from the midline of the body. Proximal means toward the trunk of the body, or toward the user. Distal means away from the trunk of the body, or away from the user.

In this specification, a standard system of three mutually perpendicular reference planes is employed. A sagittal plane divides a body into bilaterally symmetric right and left portions. A coronal plane divides a body into anterior and posterior portions. A transverse plane divides a body into superior and inferior portions.

In this specification, standard knee anatomical terms are employed with their ordinary and customary meanings.

The systems, methods, and devices described herein may improve a surgeon's likelihood of matching an ACL graft to a natural ACL attachment area on a femur or tibia; improve graft fixation; reduce surgical time; and improve clinical outcomes.

As used in this specification with reference to one or more structures, the terms "engaged," "engaged with," "coupled," or "coupled to," can mean that the one or more structures are engaged (or coupled) with each other either directly, or through one or more intermediate members.

It will be understood that the terms "ligament" or "ligament graft" as used herein, include any type of ligament graft including, but not limited to: any artificial ligament graft, natural ligament graft, allograft, autograft, xenograft, tendon, etc.

The following disclosure focuses on ligament graft repair of the ACL ligament. However, it will be understood that the devices, systems, methods, and instrumentation disclosed herein can be used in other ligament repair applications including, but not limited to: Posterior Cruciate Ligament (PCL), shoulder, ankle, foot, elbow, wrist, fingers, hands, back, neck, arms, legs, hips, etc.

FIGS. 1-4 show various views of a surgical tool 1 that facilitates both the preparation and insertion of a ligament graft 10 into a patient. The surgical tool 1 can apply tension to the ligament graft 10 to keep the ligament graft 10 straight and close to a shaft, or elongate member 12 of the surgical tool 1 to help facilitate insertion of the ligament graft 10 into the patient. The surgical tool 1 can also help prepare the ligament graft 10 for insertion into the patient by applying a tension force to the ligament graft 10 to help "exercise" the ligament graft 10 prior to insertion.

Exercising or "pre-stretching" a ligament graft reduces the likelihood of post-operative ligament creep. Ligament creep is the undesirable lengthening or "stretching-out" of the ligament graft after it is has been implanted in the patient. In order to reduce the likelihood of ligament creep, the surgeon will typically exercise the ligament graft by applying a constant tension force to the ligament graft for a period of time sufficiently long enough to stretch out the ligament such that any additional stretching results in little or no lengthening of the ligament. Typically, the surgeon will stretch out the ligament with one device, remove the ligament from the stretching device, and then use a second device to insert the ligament into the patient. Switching the ligament between two separate devices is inefficient; increases the duration of the surgical procedure; and increases the risk of surgical complications. Moreover, once the ligament graft is released from the stretching device, the ligament is free to relax and shorten again over time, thereby increasing the likelihood of reintroducing ligament creep. Thus, the surgeon has to try to insert the ligament graft into the patient as quickly as possible, hoping that the ligament remains sufficiently "exercised" that little or no creep occurs. The surgical tool 1 shown in FIGS. 1-4 eliminates these problems by providing a single tool 1 that can be used to both exercise the ligament graft and insert the ligament graft into the patient while maintaining the ligament graft under tension throughout the entire procedure.

FIG. 1 shows the surgical tool 1 holding a ligament 10 under tension. In this example, a fixation device, or aperture plug 14, is attached to the distal end of elongate member 12. The ligament 10 can be wrapped around the aperture plug 14 and connected to attachment members 4, 6 through sutures 20, 22 engaged with each end of the ligament 10. Tension forces applied to the ligament 10 can be increased by rotating a twist knob 8 in a first direction causing the shaft 12 to move in the distal direction and stretching the ligament 10. Tension forces applied to the ligament can also be reduced by rotating the twist knob 8 in a second direction causing the shaft 12 to move in the proximal direction allowing the ligament 10 to relax. In the example shown in FIG. 1, the aperture plug 14 is also connected to a cortical fixation system which includes a cortical fixation member 16 and at least one connector 18.

Figure 2:
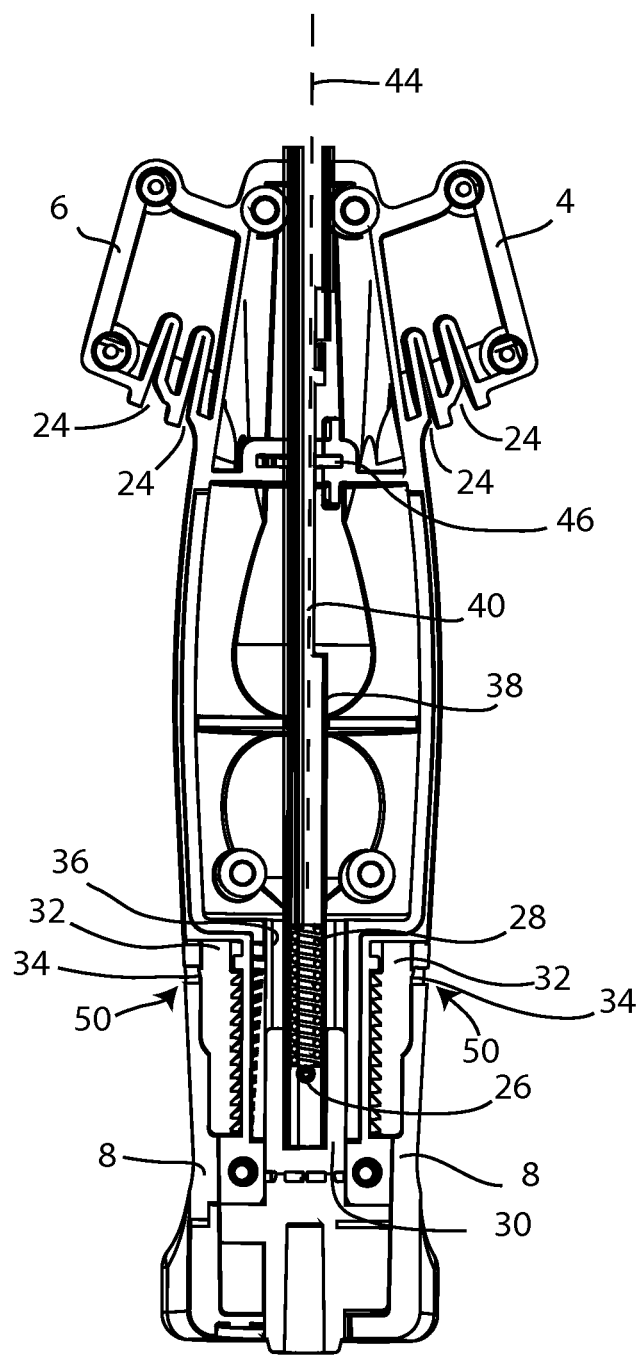
FIG. 2 is a cross-sectional side view of the handle portion 2 of the surgical tool 1 of FIG. 1 with the cross-sectional plane taken parallel to the two attachment members 4, 6 along their greatest width.

Continuing with FIG. 1, the distal end of the elongate member 12 can have a fixation device attachment feature (not shown) adapted to receive the fixation device 14, such as a protrusion configured for insertion into an aperture formed in the fixation device 14. Alternatively, the fixation device attachment feature can be threading formed on the elongate member 12 with complimentary shaped threading formed in the plug 14. The elongate member 12 has a longitudinal axis 44, as seen in FIG. 2. The cross-sectional area of the elongate member 12 can be less than the cross-sectional area of the fixation device 14 attached to the elongate member 12, with both cross-sectional areas taken transverse the longitudinal axis 44.

A handle portion 2 can also include an impact surface located on the proximal end of the surgical tool 1 configured to receive impact forces to help drive the aperture plug 14 into the bone tunnel.

In other examples, a fixation device, or aperture plug 14, may not be used. Instead, the distal end of the elongate member 12 can include a notch or groove (not shown) to receive a portion of the ligament 10 for tensioning.

In another embodiment (not shown), one or more of the attachment members 4, 6 can translate in the proximal and distal directions relative to the handle portion 2 to apply tension to the ligament 10, instead of, or in addition to, the elongate member 12 translating in the proximal and distal directions.

In another embodiment, the surgical tool 1 can include four attachment members (not shown) configured to tension two ligaments 10 at the same time forming a "quadruple bundle" ACL repair graft.

A method of using the surgical tool 1 shown in FIGS. 1-4 will now be described in the context of repairing an ACL with the aperture plug 14 inserted into the femur of the patient. However, it will be understood that this apparatus, system, and method can be applied in other ligament reconstruction procedures, as mentioned previously. A surgeon can obtain a suitable ligament graft 10 and attach sutures 20, 22 to each end of the ligament graft 10 using known methods in the art, such as "whip-stitching." The surgeon can also attach a suitable aperture plug 14 to the distal end of the shaft 12. In this example, the aperture plug 14 also is attached to a cortical fixation system including a cortical fixation member 16 and at least one connector 18. The surgeon can attach one end of the ligament graft 10 to the attachment member 4 by inserting the suture 20 engaged with the end of the ligament graft, into a ligament graft attachment feature, such as a slit 24, formed in the attachment member 4. The surgeon can then wrap the ligament graft 10 around the aperture plug 14 and connect the other end of the ligament graft 10 to the opposite attachment member 6 by inserting the suture 22 into the ligament graft attachment feature 24 formed in the opposite attachment member 6. However, in other examples, the ligament can be engaged directly by the ligament graft attachment feature, which may be a clamping device to grab the ligament, or the ligament can wrap around the ligament graft attachment feature to secure the ligament to the attachment feature. The surgeon can then twist knob 8 in a first direction causing the shaft 12 to move in the distal direction to stretch the ligament 10. The surgeon can select how much tension force is applied to the ligament graft 10 as he/she rotates the twist knob 8. In one example, the surgeon can select about 22 pounds of tension force. The selected tension force can be applied to the graft 10 and maintained for a predetermined amount of time sufficient to "exercise" the ligament graft 10 and reduce or eliminate ligament creep. The surgeon can then insert the entire ligament graft system into the patient starting with the cortical fixation connector 18. The surgeon can thread the connector 18 and cortical fixation member 16 through a tibial bone tunnel (not shown), and then into a femoral bone tunnel (not shown) formed in the patient, until the cortical fixation member 16 passes through the femoral bone tunnel. The aperture plug 14 and ligament graft follow the cortical fixation system as it is inserted, passing through the tibial bone tunnel and into the femoral bone tunnel. The surgeon can rotate the surgical tool 1 to orient the placement of the aperture plug 14 within the femoral tunnel. The surgeon can also use impact forces transmitted through the handle portion 2 of the surgical tool 1 to force the aperture plug 14 into the femoral bone tunnel. Once the aperture plug 14 is at the desired location within the femoral bone tunnel, the surgeon can adjust the length of the connector 18 to remove any slack between the cortical fixation member 16 and the aperture plug 14. The surgeon can then attach the cortical fixation member 16 to the cortical bone of the femur. This process is known in the surgical arts as "cortical fixation." In this manner, the aperture plug 14 becomes "suspended" within the femoral bone tunnel by the cortical fixation system. This process is known in the surgical arts as "suspensory fixation." The surgeon can then release the sutures 20, 22 from slits 24 and remove the surgical tool 1. However, in other embodiments, the surgeon can remove the shaft 12 of the tool 1 through the proximal end of the surgical tool 1 leaving the sutures 20, 22 attached to the surgical tool 1. This allows the surgeon to maintain tension force on the ligament 10 during the remainder of the operation. The surgeon can then insert a suitable tibial plug (not shown) into the tibial bone tunnel to anchor the ligament 10 within the tibial tunnel. The surgeon can also use cortical fixation on the tibial cortical bone to "cortically-suspend" the tibial plug within the tibial bone tunnel.

Figure 3:
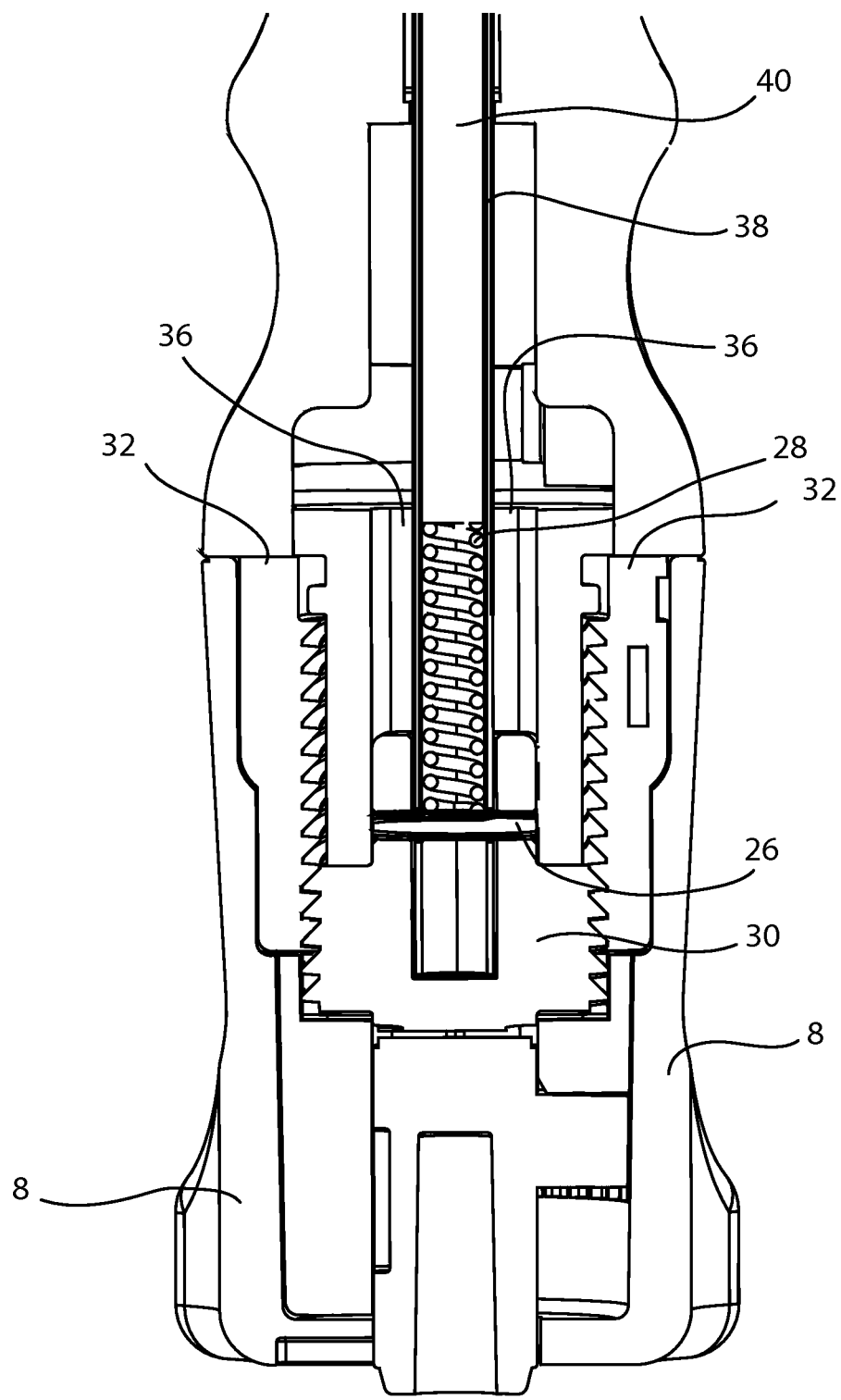
FIG. 3 is a cross-sectional side view of the handle portion 2 of the surgical tool 1 of FIG. 1 with the cross-sectional plane taken between the two attachment members 4, 6 and normal to the cross-sectional plane of FIG. 2.
Figure 4:
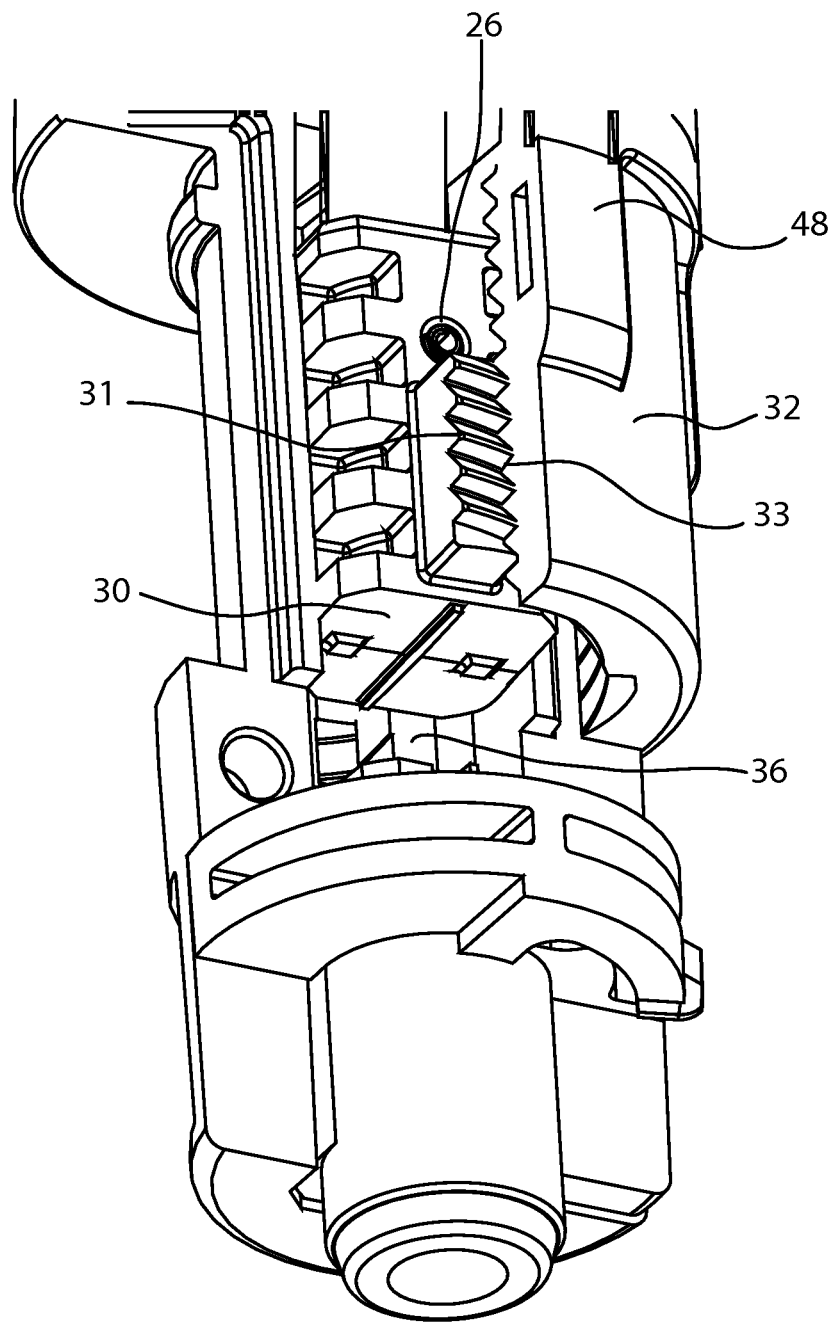
FIG. 4 is a perspective view of the proximal handle portion 2 with the twist knob removed.

The inner workings of the surgical tool 1 will now be explained with reference to FIGS. 2-4. FIG. 2 is a cross-sectional side view of the handle portion 2 of the surgical tool 1 of FIG. 1 with the cross-sectional plane taken parallel to the two attachment members at their greatest width 4, 6. FIG. 3 is a cross-sectional side view of the handle portion 2 of the surgical tool 1 of FIG. 1 with the cross-sectional plane taken between the two attachment members 4, 6 and normal to the cross-sectional plane used to generate FIG. 2. FIG. 4 is an isometric view of the proximal handle portion 2 with the twist knob 8 removed.

Twist knob 8 can slide over and attach to translator member 32. The translator member 32 can have one or more ribs 48 (see FIG. 4) configured to fit in complimentary shaped slots or depressions formed in the interior surface of the twist knob 8 (not shown). Thus, rotating the twist knob 8 will cause the translator member 32 to rotate by imparting rotational torque forces on the translator member 32 via the interface between the slots formed in the twist knob 8 and the ribs 48 of the translator member 32. The twist knob 8 can be reversibly attached to the translator member 32 via retaining members or protrusions 34 (see FIG. 2) formed on the translator member 32 that can "snap-fit" into apertures 50 formed in the twist knob 8, as the twist knob 8 slides onto the translator member 32 during assembly. The translator member 32 can have threads 33 (see FIG. 4) formed on an inner surface of the translator member 32 and configured to interact with complimentary shaped threads 31 formed on the plunger 30. Thus, rotating the twist knob 8 and translator member 32 assembly will cause the plunger 30 to translate within the elongate chamber 36 in either the proximal or distal directions. If the twist knob 8 is rotated in a first direction, the plunger 30 will move in the distal direction. If the twist knob 8 is rotated in a second direction, the plunger 30 will move in the proximal direction.

Alternatively, a ratcheting mechanism (not shown) can be used instead of rotating the plunger with threads 31, 33. In this example, the surgeon can push the plunger 30, or a member engaged with the plunger 30, in the distal direction whereupon one-way ratcheting teeth (not shown) can prevent the plunger 30 from moving backward in the proximal direction. In this manner, the ratcheting mechanism will allow the surgeon to apply and maintain tension forces on the ligament. A ratchet release mechanism (not shown) can also be used to selectively disengage the one-way ratcheting teeth, allowing the plunger 30 to move in the proximal direction, releasing the tension forces applied to the ligament 10.

Continuing with FIGS. 2-4, the elongate member 12 can have both an inner shaft 40 and an outer shaft 38. The plunger 30 can be engaged with the proximal end of the outer shaft 38 through a plunger pin 26 and the inner shaft 40 can be free to slide back and forth within the outer shaft 38. A tension member 28, such as a spring, can be placed inside the proximal end of the outer shaft 38, between the pin 26 and the proximal end of the inner shaft 40. The spring 28 pushes the inner shaft 40 in the distal direction as the plunger 30 and plunger pin 26 move in the distal direction. When a ligament 10 is placed on the surgical tool 1, as shown in FIG. 1, the ligament 10 will resist the inner shaft 40 moving in the distal direction, causing the spring 28 to compress as the plunger 30 advances in the distal direction, putting tension forces on the ligament 10 which are proportional to the amount of spring 28 compression.

The spring 28 can be chosen to exert a predetermined range of tension forces on the ligament 10. The plunger 30 can be translated far enough in the proximal direction such that the spring 28 is not compressed between the inner shaft 40 and the pin 26, and little or no tension forces are transmitted to the ligament 10. However, as the plunger 30 advances in the distal direction, the spring 28 is compressed between the inner shaft 40 and the pin 26 forcing the inner shaft 40 in the distal direction and applying tension forces on the ligament 10. The amount of tension force applied to the ligament 10 depends on how far the user chooses to translate the plunger 30 in the distal direction by rotating twist knob 8. In this manner, the amount of tension force applied to the ligament 10 varies from zero to a predetermined maximum force necessary to completely compress the spring 28. In one example, the spring 28 is chosen to exert a predetermined range of tension forces on the ligament 10 in the range of zero to about 22 pounds of force when the spring 28 is completely compressed. However, different tension members 28, or springs, can be chosen based on the particular application and range of tension forces desired.

The plunger 30 can be configured to continue translating in the distal direction even after the spring 28 is fully compressed, imparting even greater tension forces on the ligament 10 above the maximum force of the spring 28. The inner shaft 40 can also have a distal stop member 42 which interfaces with the outer shaft 38 to push the inner shaft 40 further in the distal direction, irrespective of the spring 28, to impart even greater tension forces on the ligament 10, as desired.

The inner and outer shafts 40, 38 can also be notched and held in place by a holding member 46 residing within the notches formed in the inner and outer shafts 40, 38, as can be seen in FIG. 2. In this manner, the holding member 46 can prevent the inner and outer shafts 40, 38 from rotating with respect the handle portion 2 and/or translating too far in the proximal and distal directions. The holding member 46 can also prevent the accidental removal of the inner shaft 40 from the outer shaft 38.

Figure 5A:
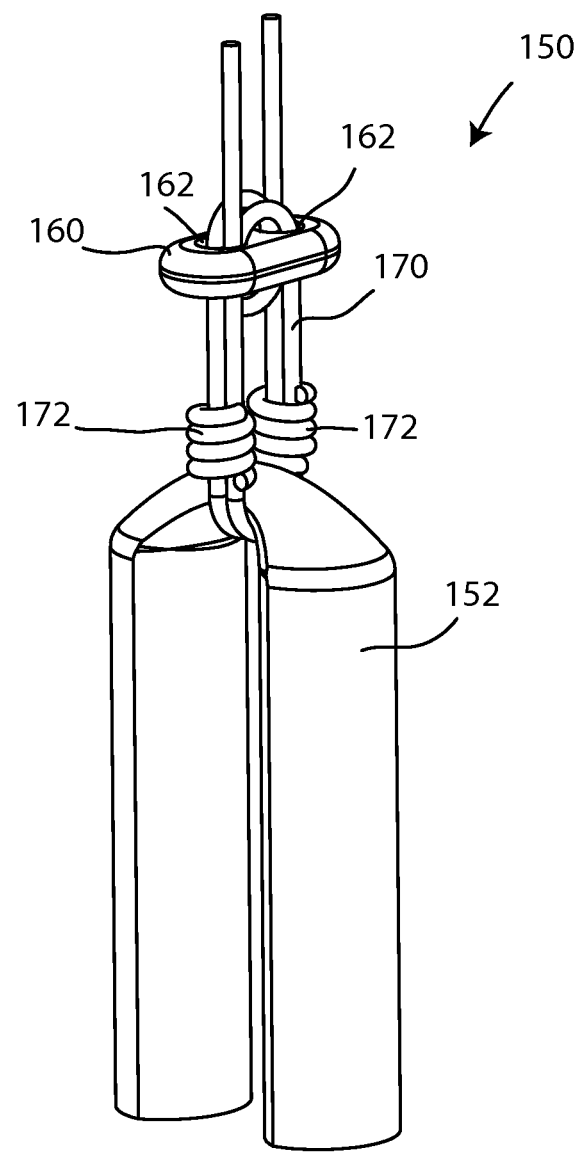
FIG. 5A is a perspective view of a ligament fixation system.

Referring to FIG. 5A, a ligament fixation system 150 is illustrated. Ligament fixation system 150 may include a first fixation device 152, a second fixation device 160, and a connector 170. One or more filaments (not shown) may also be included to help orient the second fixation device 160, as it is passed through the bone tunnel. The first fixation device 152 may be an aperture plug, the second fixation device 160 may be an extracortical button, and the connector 170 may be a flexible loop. The first fixation device 152 can be any style, size, or shape aperture plug. The system 150 may be implanted in a distal femur so that the button 160 may rest on an extracortical surface of a femur, the plug 152 may reside in a femoral bone tunnel near the original femoral attachment area of the anterior cruciate ligament, and the loop 170 may connect the button 160 to the plug 152. The loop 170 to button 160 connection and the loop 170 to plug 152 connection may resemble pulley connections. The loop 170 may be adjustable in length, and the adjustment may be made after the system 150 has been implanted. For example, the button 160 and/or plug 152 may include features, such as slits or passageways, which interact with the loop 170 to permit adjustment. One way or two way adjustment is contemplated. For example, the loop 170 may be shortenable, and may be lockable to prevent lengthening. In another example, the loop 170 may be lengthenable, and may be lockable to prevent shortening. In yet another example, the loop 170 may be shortenable and lengthenable, and may be lockable once a desired length is achieved. Locking may be selectable or automatic.

In an alternate embodiment, the ligament fixation system 150 may include a fixation device 160, a connector 170, and a ligament graft attached directly to the connector 170 without an aperture plug. The fixation device 160 may be an extracortical button, and the connector 170 may be a flexible member. The system 150 may be implanted in a distal femur so that the button 160 may rest on an extracortical surface of a femur. The graft may reside in a femoral bone tunnel and occupy the original femoral attachment area of the anterior cruciate ligament, and the connector 170 may connect the button 160 to the graft by suspensory fixation. The button 160 may include a plurality of apertures 162 through which the connector 170 may be routed. The connector 170 may be a line, suture, cord, cable, wire, filament, or the like. The way that the connector 170 is routed through the button 160 may cause the connector 170 to behave as if connected to the button by one or more pulleys. The connector 170 may be routed through the button 160 to form a loop, which may be adjustable to lengthen and/or shorten the loop. The connector 170 may include one or more locking portions 172 which may selectively or automatically lock the connector 170 once a desired length is achieved. The locking portions 172 may resemble a finger trap or a sliding knot, and may function to lock separate portions of the connector 170 together.

Figure 5B:
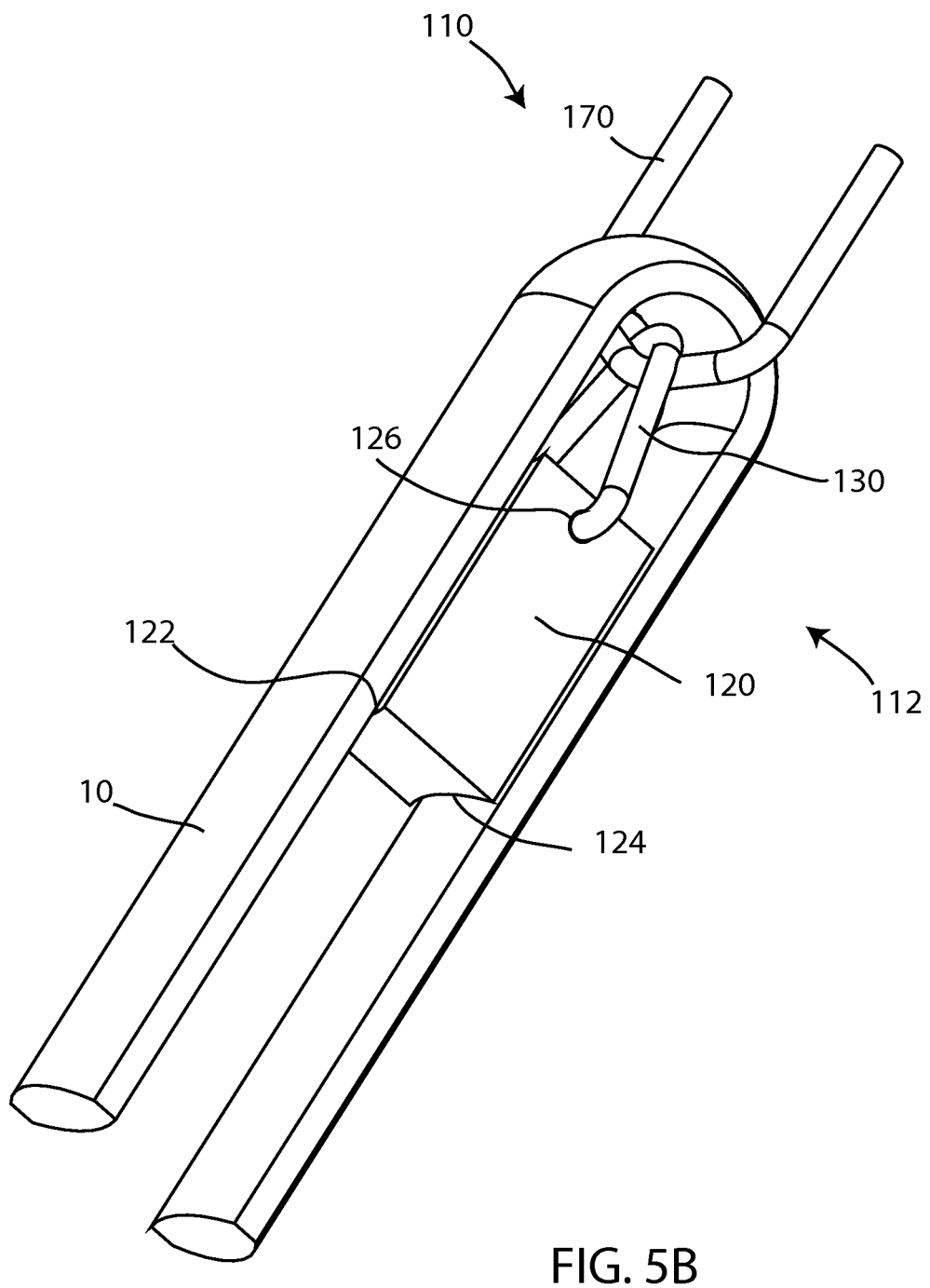
FIG. 5B is a perspective view of another ligament fixation system.

Referring to FIG. 5B, another ligament fixation system 110 is shown with a ligament graft 10. A first fixation device 112 may include a body 120 and a tether 130. The body 120 may be an aperture plug with a pair of opposing grooves 122, 124 in which the graft 10 rests in use. The body 120 may include an aperture 126 to receive the tether 130. The tether 130 may flexibly connect the body 120 to the connector 170. For example, the tether 130 may be a flexible loop threaded through the aperture 126 and the connector 170. First fixation device 112 may be used with the loop 170, button 160, and graft 10 in a manner similar to that described in FIG. 5A.

Figure 6A:
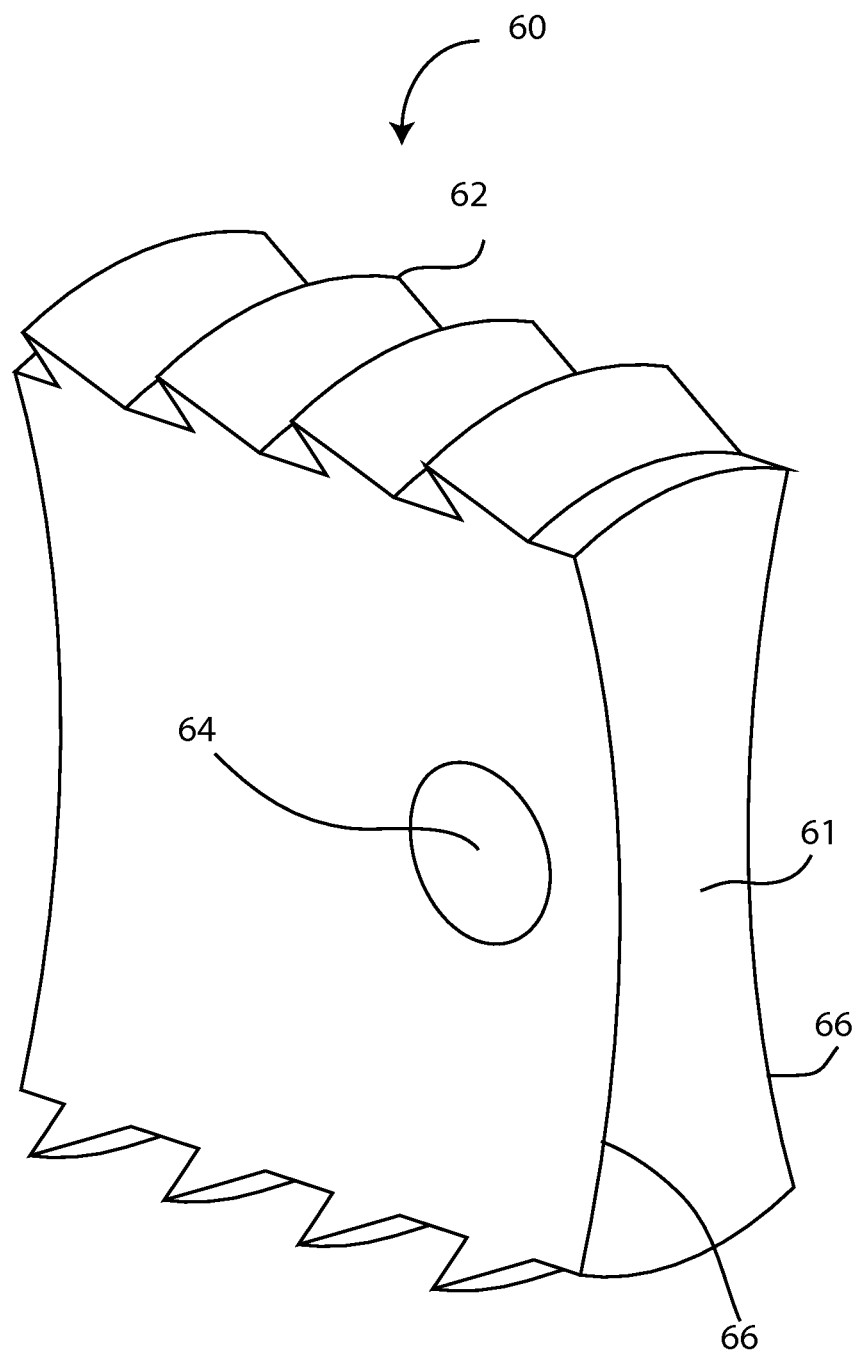
FIG. 6A is a perspective view of a fixation device.
Figure 6B:
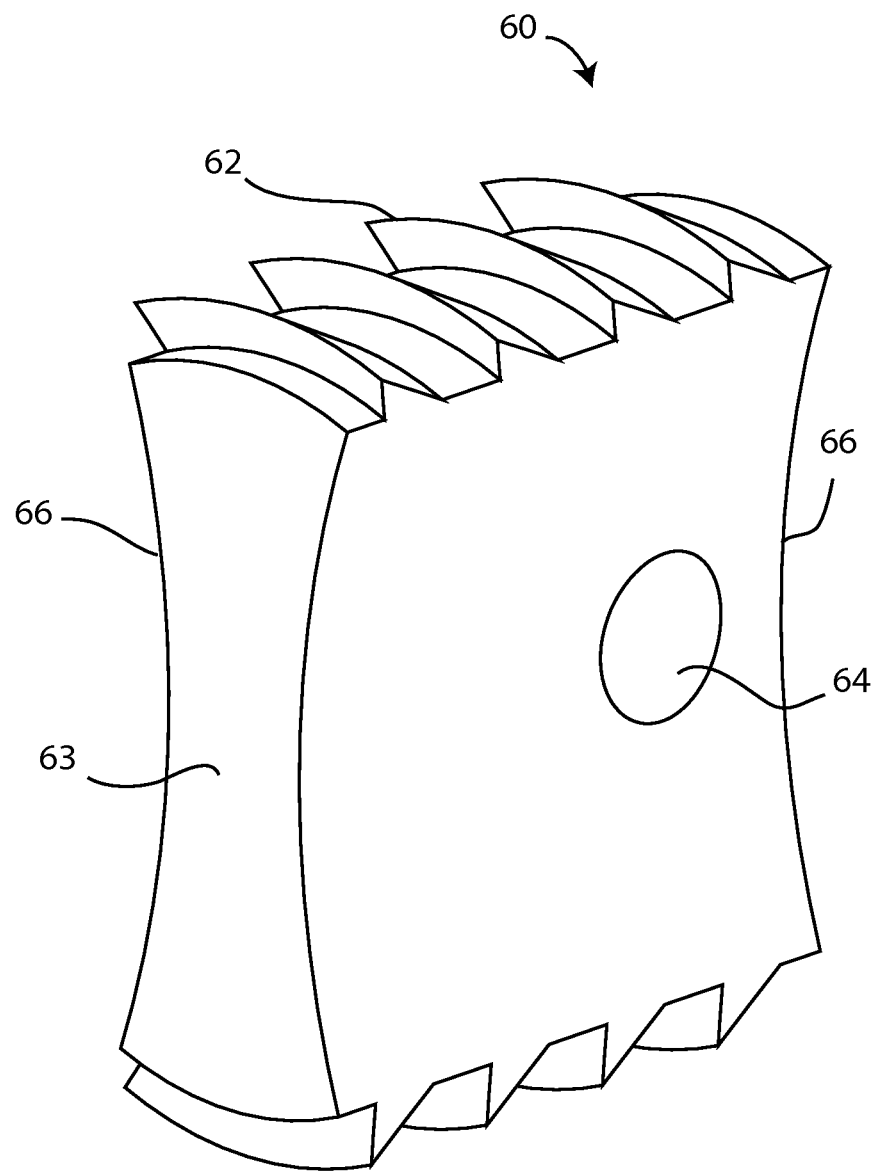
FIG. 6B is another perspective view of the fixation device of FIG. 6A from a different angle.

Referring to FIGS. 6A and 6B, another fixation device 60 is shown in front and back perspective views. The first fixation device 60 may be an aperture plug which extends from a leading end 61 to a trailing end 63. The first fixation device 60 may include a pair of opposing grooves 66 which extend between the leading end 61 and the trailing end 63. The first fixation device 60 may include opposing sets of protrusions 62 between the grooves 66. The protrusions 62 may be barbs, ridges, teeth, serrations, posts, ribs, or the like. One or more apertures 64 may extend through the first fixation device 60. In use, the first fixation device 60 may be implanted in a bone tunnel with the loop 170 threaded through the aperture 64 to connect the first fixation device 60 to the extracortical button 160. The graft 10 may lie in the grooves 66 and the protrusions 62 may engage the bone tunnel. The first fixation device 60 may also be used without the loop 170 or button 160.

Figure 6C:
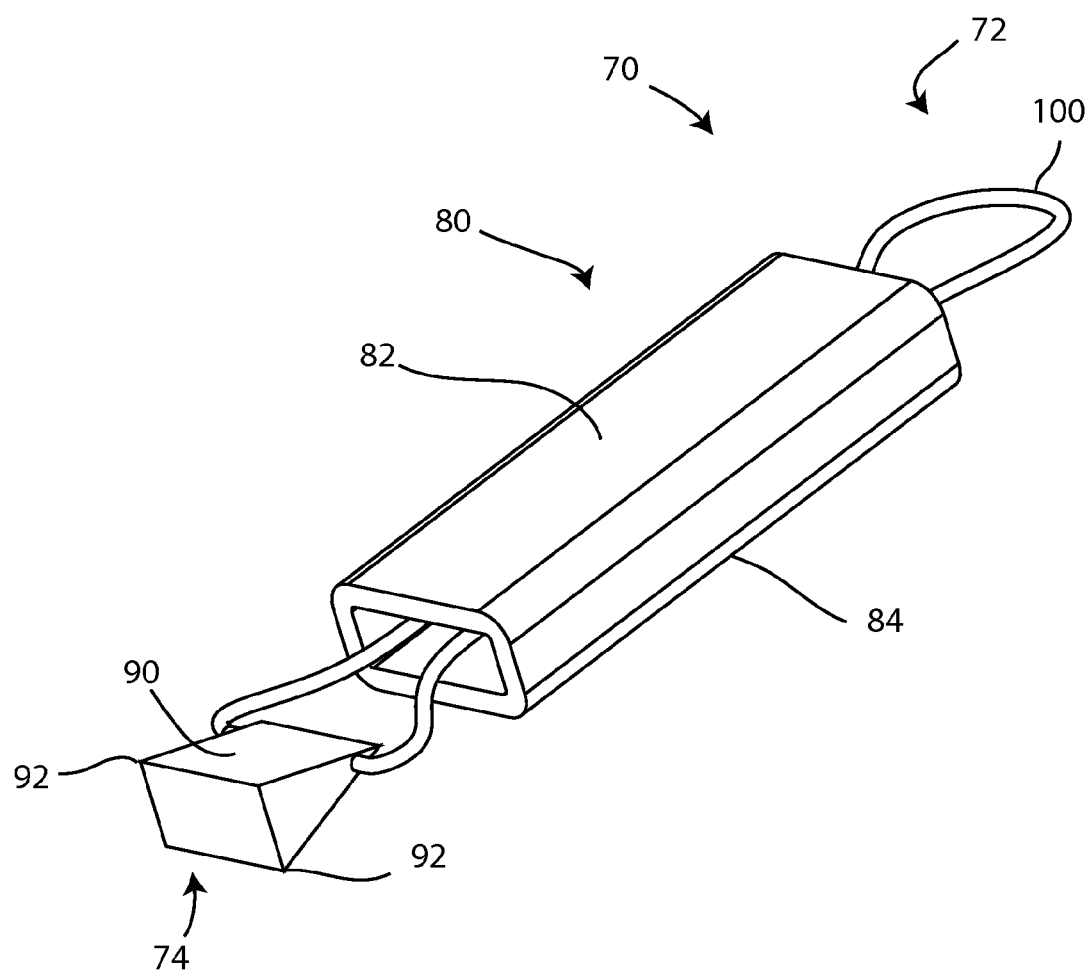
FIG. 6C is a perspective view of another fixation system.
Figure 6D:
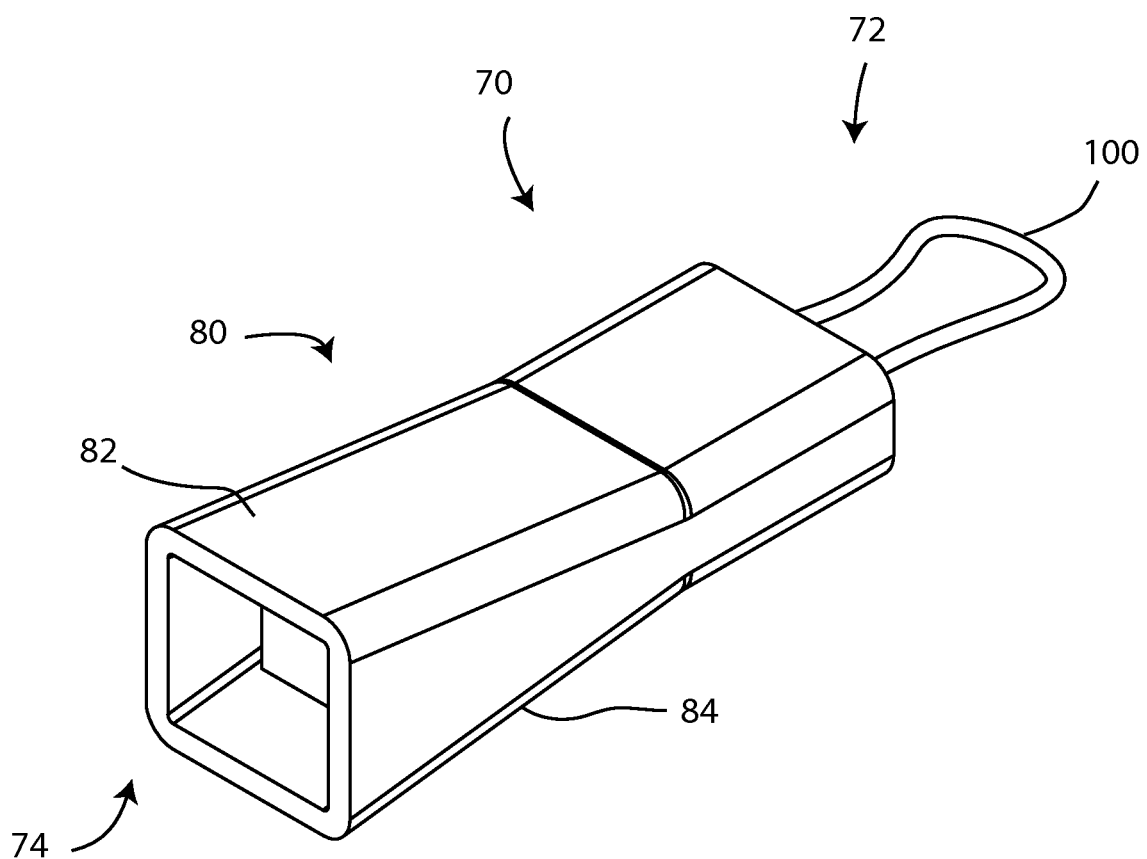
FIG. 6D is another perspective view of the fixation system of FIG. 6C in an expanded configuration.

Referring to FIGS. 6C and 6D, yet another fixation device 70 is shown. The first fixation device 70 may be an aperture plug system, and may extend from a leading end 72 to a trailing end 74. The first fixation device 70 may include an expanding element 80, an expander 90, and an actuation element 100. The expanding element 80 may be a sheath, a sleeve, a tube, or the like. The expander 90 may be a wedge or the like. The actuation element 100 may be used to urge the expander 90 into engagement with the expanding element 80 to cause expansion of the expanding element 80. The actuation element 100 may pull, push, twist, or otherwise urge the expander 90 into engagement with the expanding element 80. In the example shown, the actuation element 100 is a tension element such as a line, suture, cord, cable, wire, filament, or the like. The actuation element 100 may also be a compression element, such as a shaft or pole, or a torque element, such as a hex key. In use, the first fixation device 70 may be implanted in a bone tunnel with the graft 10 resting against opposite sides 82, 84 of the sleeve 80. The suture 100 may be pulled to draw the wedge 90 inside the sleeve 80, thus expanding the sleeve as shown in FIG. 6D and urging the graft 10 against the bone tunnel. The trailing corners 92 of the wedge 90 may dig into the sleeve 80 to prevent the wedge 90 from working itself out of the sleeve 80. The wedge 90 may also include other protrusions (not shown) which prevent backout. The sleeve 80 may be smooth or textured.

Figure 7A:
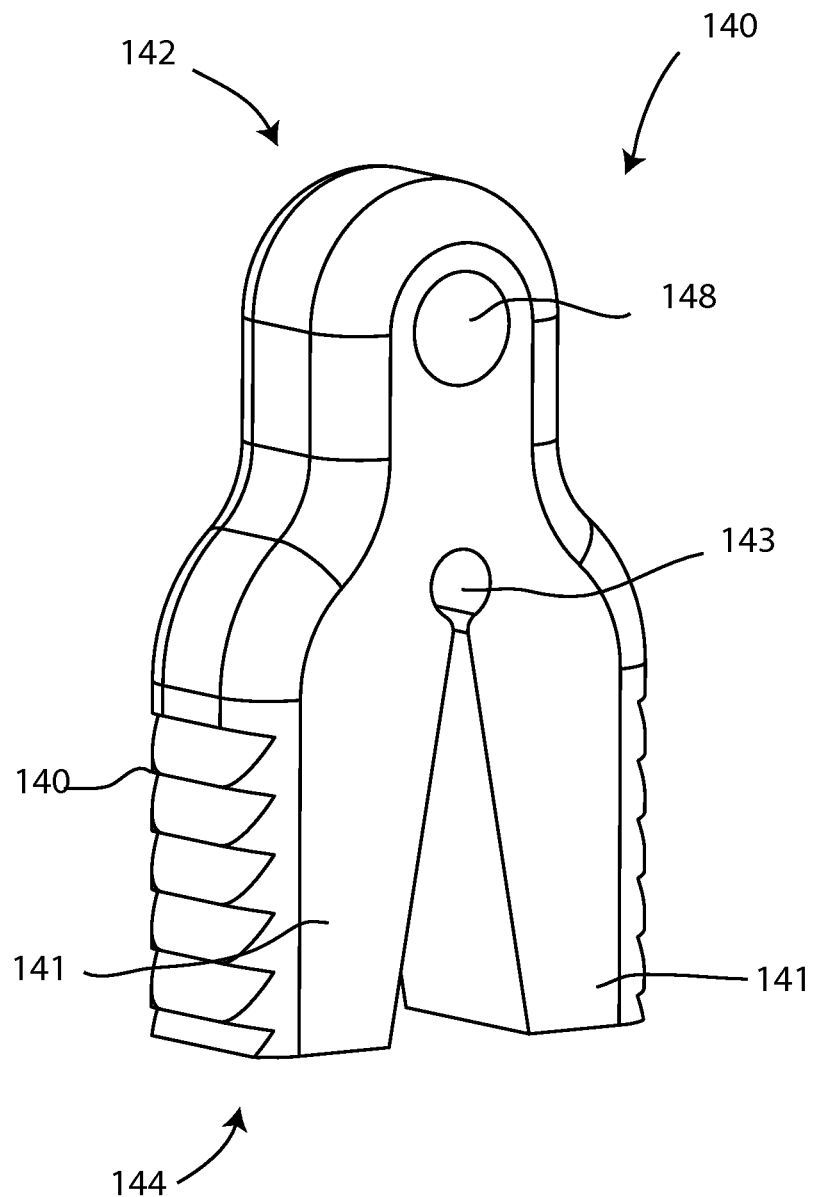
FIG. 7A is a perspective view of another fixation device.
Figure 7B:
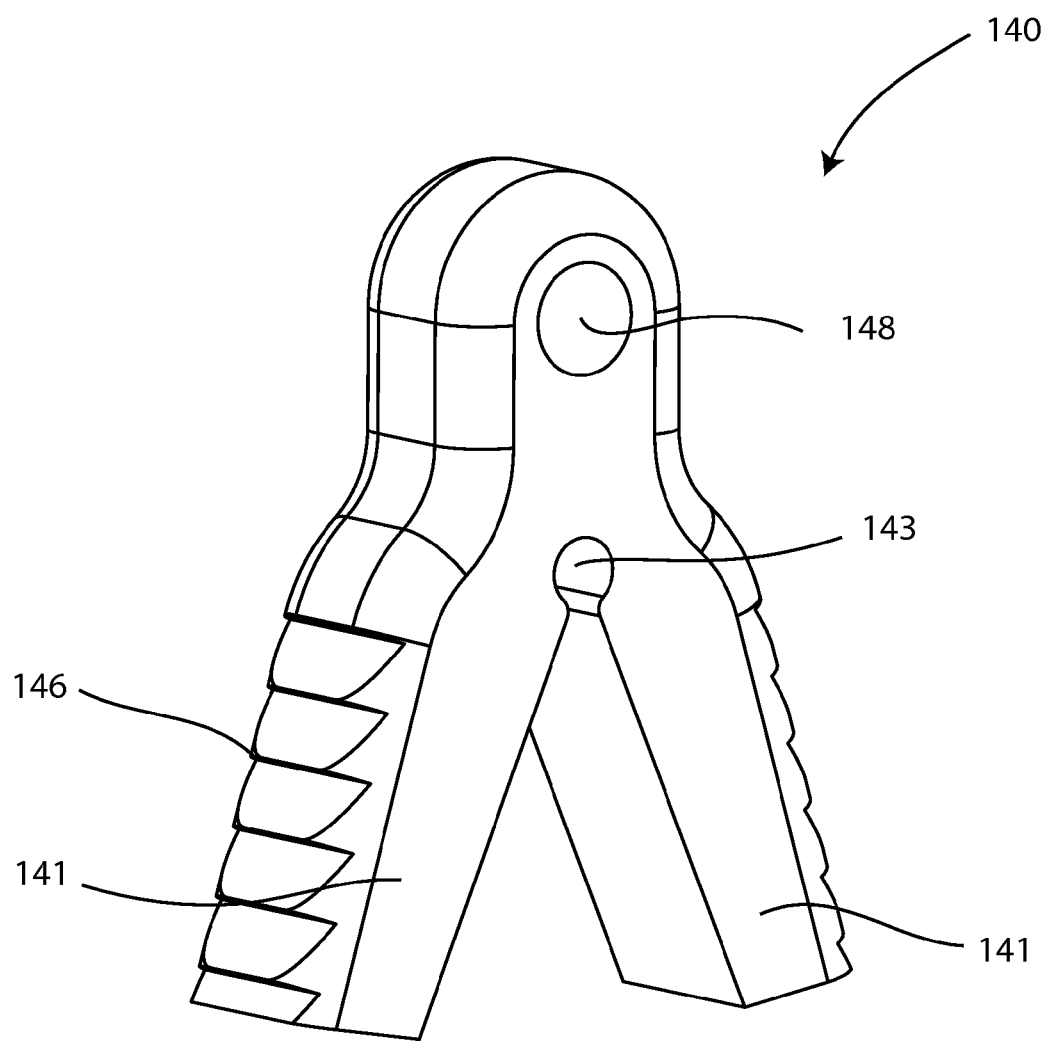
FIG. 7B is a perspective view of the fixation device of FIG. 7A in an expanded configuration.

Referring to FIGS. 7A and 7B, yet another fixation device 140 is shown. First fixation device 140 may be another aperture plug which extends from a leading end 142 to a trailing end 144. Aperture plug 140 may be at least partially split so that the trailing end 144 bifurcates into two or more bendable legs 141. The aperture plug 140 may include opposing sets of protrusions 146 on outward facing lateral surfaces of the trailing end 144. An aperture 148 may extend through the leading end 142 and the two or more legs 141 may also be separated by an aperture 143. Aperture plug 140 may be at least partially formed from a flexible or resilient material so that the trailing end 144 can assume a more closed configuration as shown in FIG. 7A, or a more open configuration, as shown in FIG. 7B. First fixation device 140 may be used with the loop 170, button 30, and graft in a manner similar to that described for first fixation device 20. In this arrangement, the loop 170 may be threaded through the aperture 148 and the graft may rest against the protrusions 146 so that the trailing end 144 tends to urge the graft against the bone tunnel wall.

Figures 8A, 8B, 8C:
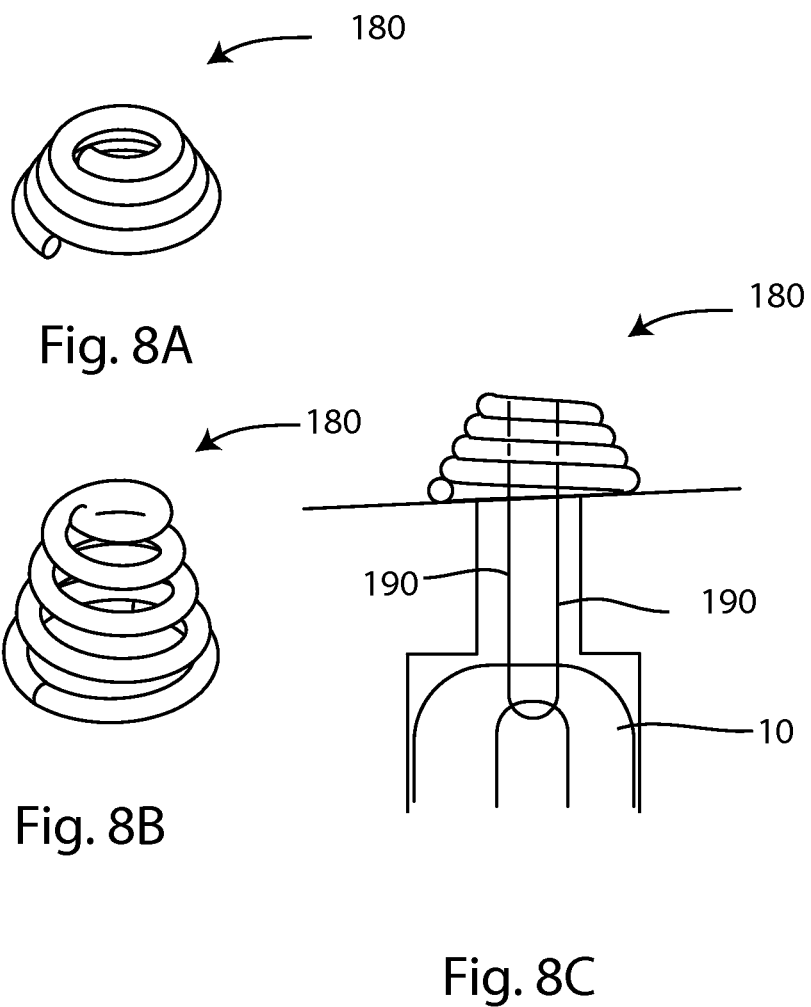
FIG. 8A is a perspective view of yet another fixation device.
FIG. 8B is a perspective view of the fixation device of FIG. 8B in an uncoiled configuration.
FIG. 8C is a side cross sectional view of the fixation device of FIG. 8A in an fixation system with a graft suspended in a bone tunnel.

Referring to FIGS. 8A-8C, another fixation device 180 is shown. Second fixation device 180 may be described as an extracortical suspensory button. Button 180 may be made of a flexible or resilient material that allows it to collapse to a smaller size and expand to a larger size. For example, the button 180 is shown as a coiled structure which may have a closely packed configuration, shown in FIG. 8B, and an at least partially uncoiled configuration, shown in FIG. 8A. The uncoiled configuration may permit the button 180 to slide lengthwise through a bone tunnel, while the packed configuration may permit the button to rest on an extracortical bone surface to support the graft 10 with a connector 190, as shown in FIG. 8C. The button 180 may be made of a metal or fiber mesh which is woven and coiled to provide the described configurations and functions.

Figure 9A:
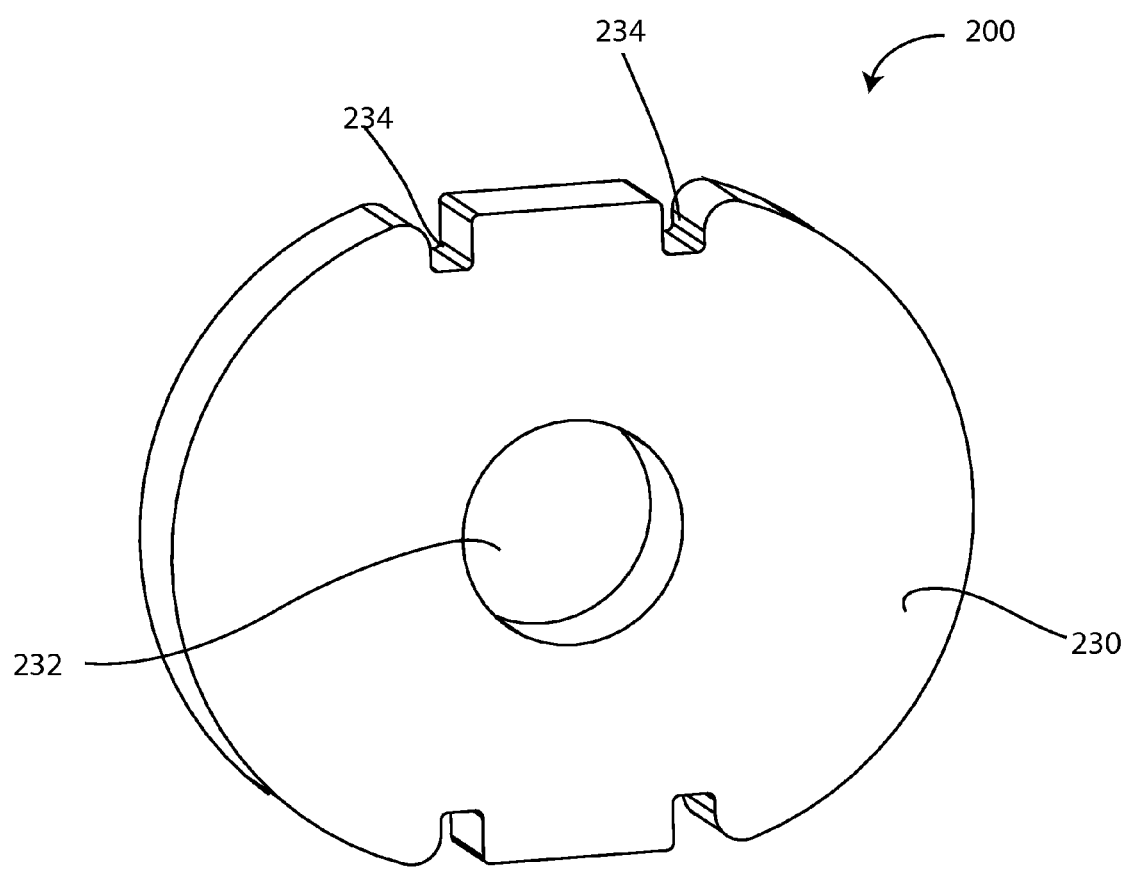
FIG. 9A is a perspective view of yet another fixation system.

Referring to FIG. 9A, a cortical fixation system 200 is illustrated. Cortical fixation system 200 can include a washer 230 and screw or screw construct (not shown). The washer 230 may be described as an extracortical button and can have an aperture 232 configured to receive the screw. The screw can be polyaxially pivotable with respect to the washer 230. The system 200 may be implanted in a proximal tibia so that the washer 230 may rest on an extracortical surface of the tibia and the screw may reside in a tibial bone tunnel which extends through an original tibial attachment area of the anterior cruciate ligament. The washer 230 may include peripheral grooves or notches 234 to receive sutures (not shown) stitched to the ends of the graft. The sutures can be tied to the washer 230 by wrapping the sutures around the washer 230 in a variety of different patterns. The grooves or notches 234 can help engage the sutures to the washer 230.

Figure 9B:
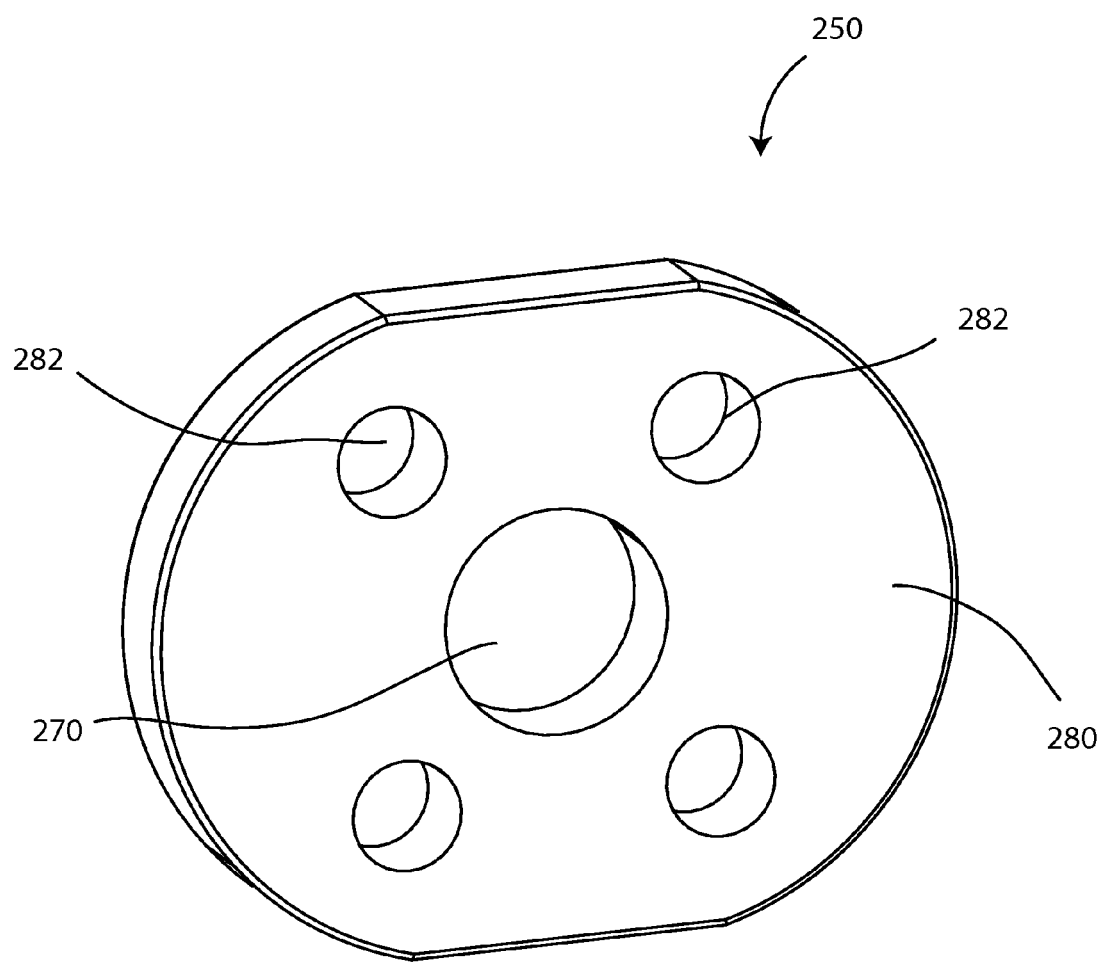
FIG. 9B is a perspective view of yet another fixation system.

Referring to FIG. 9B, another cortical fixation system 250 is shown similar to that in FIG. 9A. The washer 280 can include an aperture 270 configured to receive a screw (not shown). The system 200 may be implanted in a proximal tibia so that the washer 230 may rest on an extracortical surface of the tibia and the screw may reside in a tibial bone tunnel which extends through an original tibial attachment area of the anterior cruciate ligament. The washer 280 may also include apertures 282 for receiving sutures (not shown) stitched to the ends of the graft. The sutures can be tied to the washer 230 by threading the sutures through the apertures 282 formed in the washer 280 in a variety of different patterns. In this manner, the apertures 282 can help engage the sutures to the washer 280.

Figure 9C:
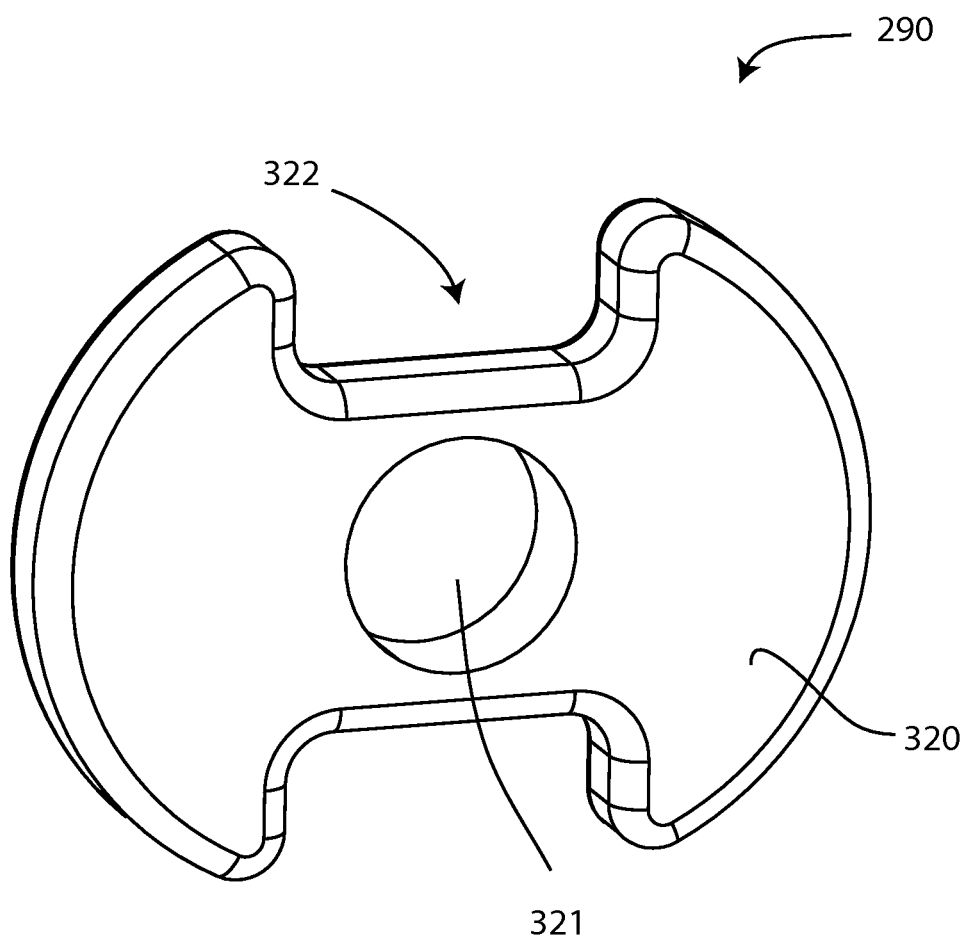
FIG. 9C is a perspective view of yet another fixation system.

Referring to FIG. 9C, yet another cortical fixation system 290 is shown similar to those above. The washer 320 can include an aperture 321 configured to receive a screw (not shown). The washer 320 may include broad peripheral grooves or notches 322 to receive the ends of the graft and/or sutures (not shown). The washer 320 may have a FIG. 8, bar, bowtie, or dogbone appearance. The sutures and/or graft can be tied to the washer 320 by wrapping the sutures around the washer 320 in a variety of different patterns. The grooves or notches 322 can help engage the sutures to the washer 320.

Figure 10A:
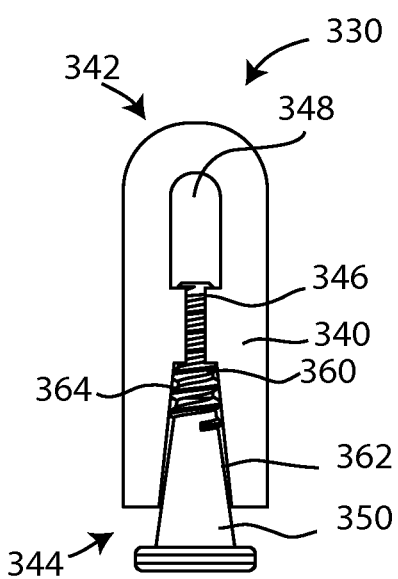
FIG. 10A is a side view of yet another fixation system.
Figure 10B:
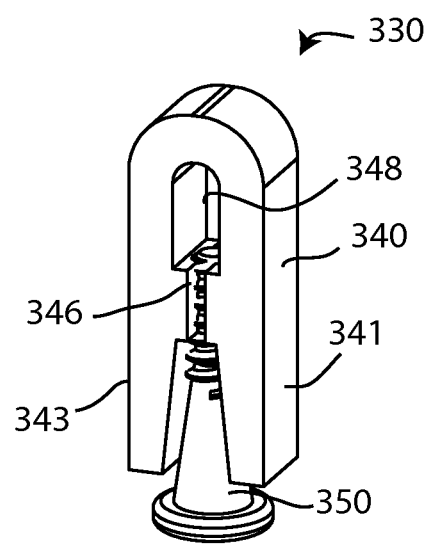
FIG. 10B is a perspective view of the fixation system of FIG. 10A.

Referring to FIGS. 10A and 10B, yet another fixation system 330 is shown. The fixation system 330 may include a first fixation device 340, a second fixation device (not shown), and a connector 350. The first fixation device 340 may be an aperture plug. The second fixation device may be an extracortical suspensory button or washer, as disclosed herein. The connector 350 may include a threaded fastener 364 which may be a self-tapping screw. The plug 340 may extend from a leading end 342 to a trailing end 344. The plug 340 may be at least partially split lengthwise so that the trailing end 344 bifurcates. The plug 340 may include a portion which forms a chamber 346 to receive the fastener 360. The plug 340 may form an aperture or eyelet 348 near the leading end 342. The second fixation device may include any of the features set forth for other washers in this disclosure. The washer may be polyaxially pivotable about a head of the connector 350. The connector 350 may include a taper or wedge 362, which may be integral with or formed separately from the threaded fastener 364. The tibial fixation system 330 may be implanted so that the washer rests against an extracortical bone surface of the proximal tibia, the plug 340 is in a bone tunnel which extends through an original tibial attachment area of the anterior cruciate ligament, and the graft (not shown) rests against side surfaces 341, 343 of the plug. As the threaded fastener 364 is advanced into the plug 340, the wedge 362 forces the trailing end 344 to expand and force the graft against the bone tunnel. However, expansion may be controlled in this system by limiting the threaded engagement with the chamber 346 and/or by providing a thread relief. Furthermore, expansion may be limited when the wedge 362 makes contact with the chamber.

The first fixation device 340 may be fabricated from polymer, metal, ceramic, bone, or other biocompatible material. In one example, the first fixation device 340 may include a solid polymer portion and a portion formed from bone. The polymer portion may be polyetheretherketone (PEEK). The solid polymer portion may form at least part of the leading end 342 and the bone portion may form at least part of the trailing end 344.

Figures 11A, 11B:
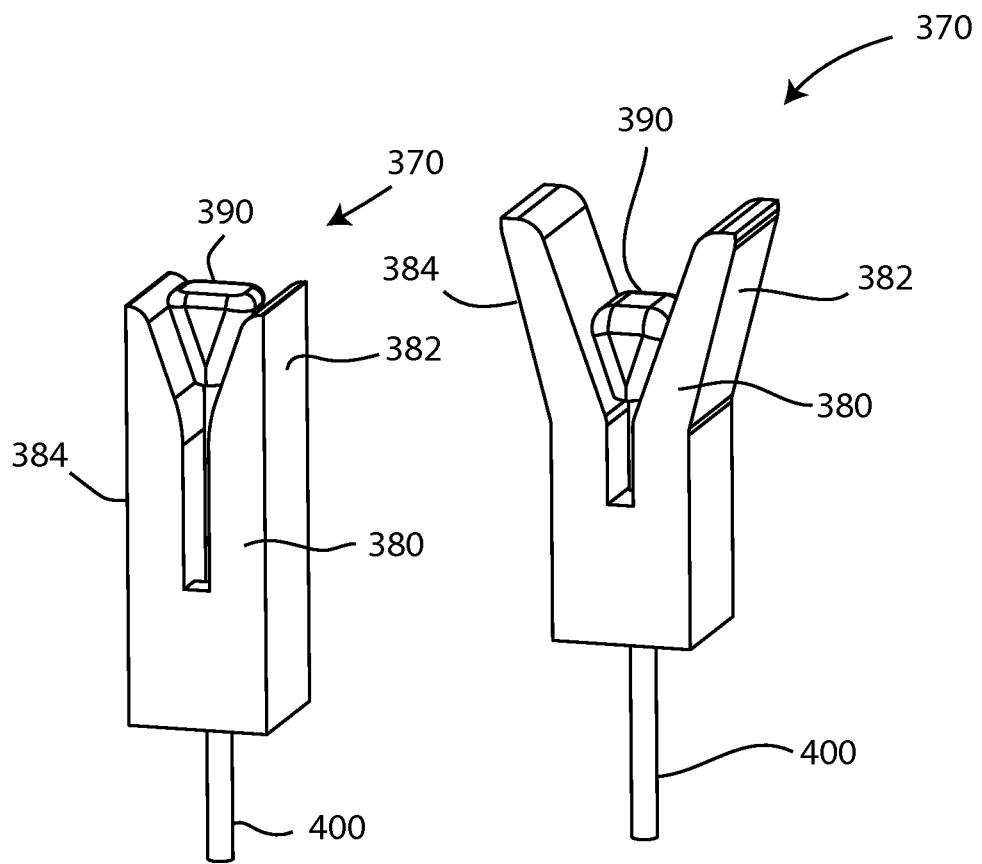
FIG. 11A is a perspective view of yet another fixation system.
FIG. 11B is a perspective view of the fixation system of FIG. 11A in an expanded configuration.

Referring to FIGS. 11A and 11B, yet another cortical fixation system 370 is shown. The cortical fixation system 370 may include an expanding element 380, an expander 390, and an actuation element 400. The expanding element 380 may be an aperture plug which is at least partially split lengthwise. The expander 390 may be a wedge, cam, or the like. The actuation element 400 may be used to urge the expander 390 into engagement with the expanding element 380 to cause expansion of the expanding element 380. The actuation element 400 may pull, push, twist, or otherwise urge the expander 390 into engagement with the expanding element 380. In the example shown, the actuation element 400 is a tension element such as a line, suture, cord, cable, wire, filament, or the like. The actuation element 400 may also be a compression element, such as a shaft or pole, or a torque element, such as a hex key. In use, the system 370 may be implanted in a bone tunnel with the graft (not shown) resting against opposite sides 382, 384 of the plug 380. The suture 400 may be pulled to draw the wedge 390 inside the plug 380, thus expanding the plug as shown in FIG. 11B and urging the graft against the bone tunnel. The wedge 390 may include protrusions (not shown) which prevent backout. The actuation element 400 may hold the wedge 390 in place permanently. The plug 380 may be smooth or textured.

Figure 12A:
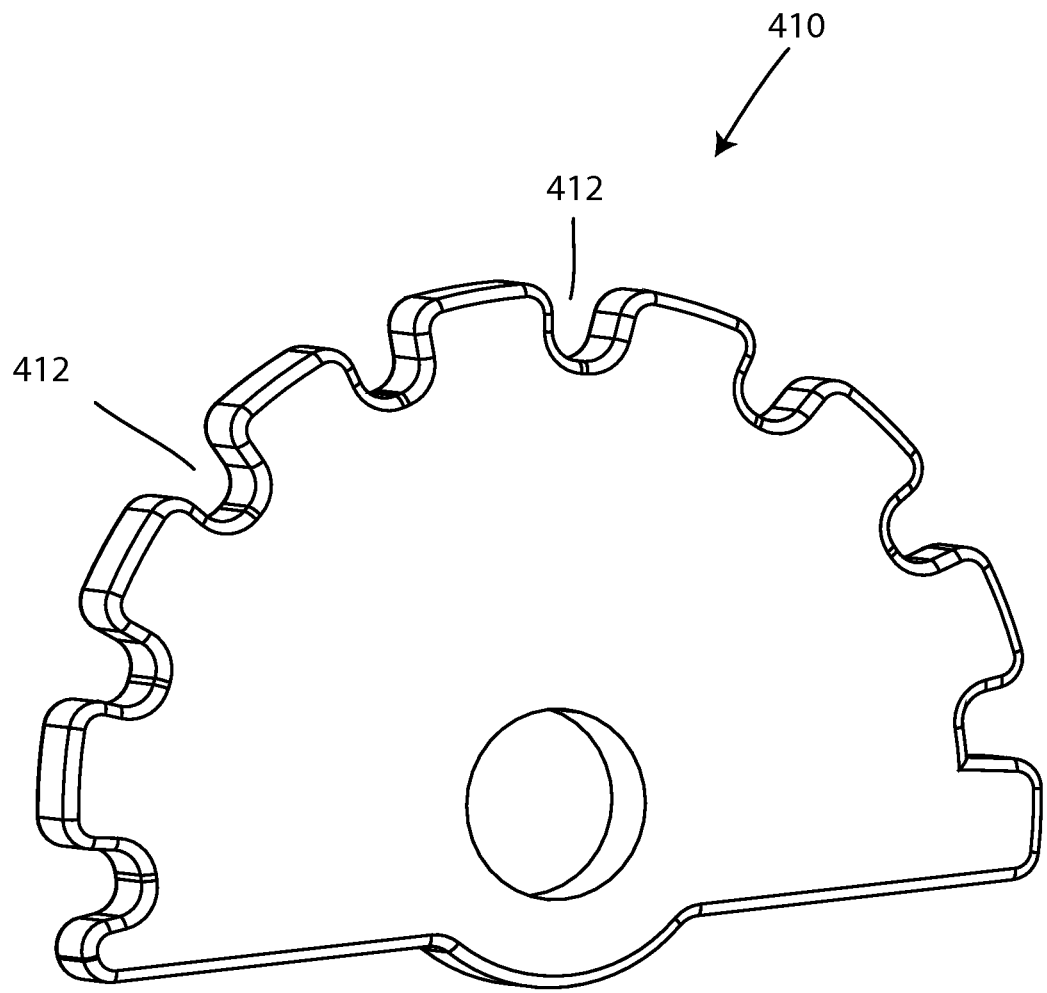
FIG. 12A is a top view of yet another fixation device.
Figure 12B:
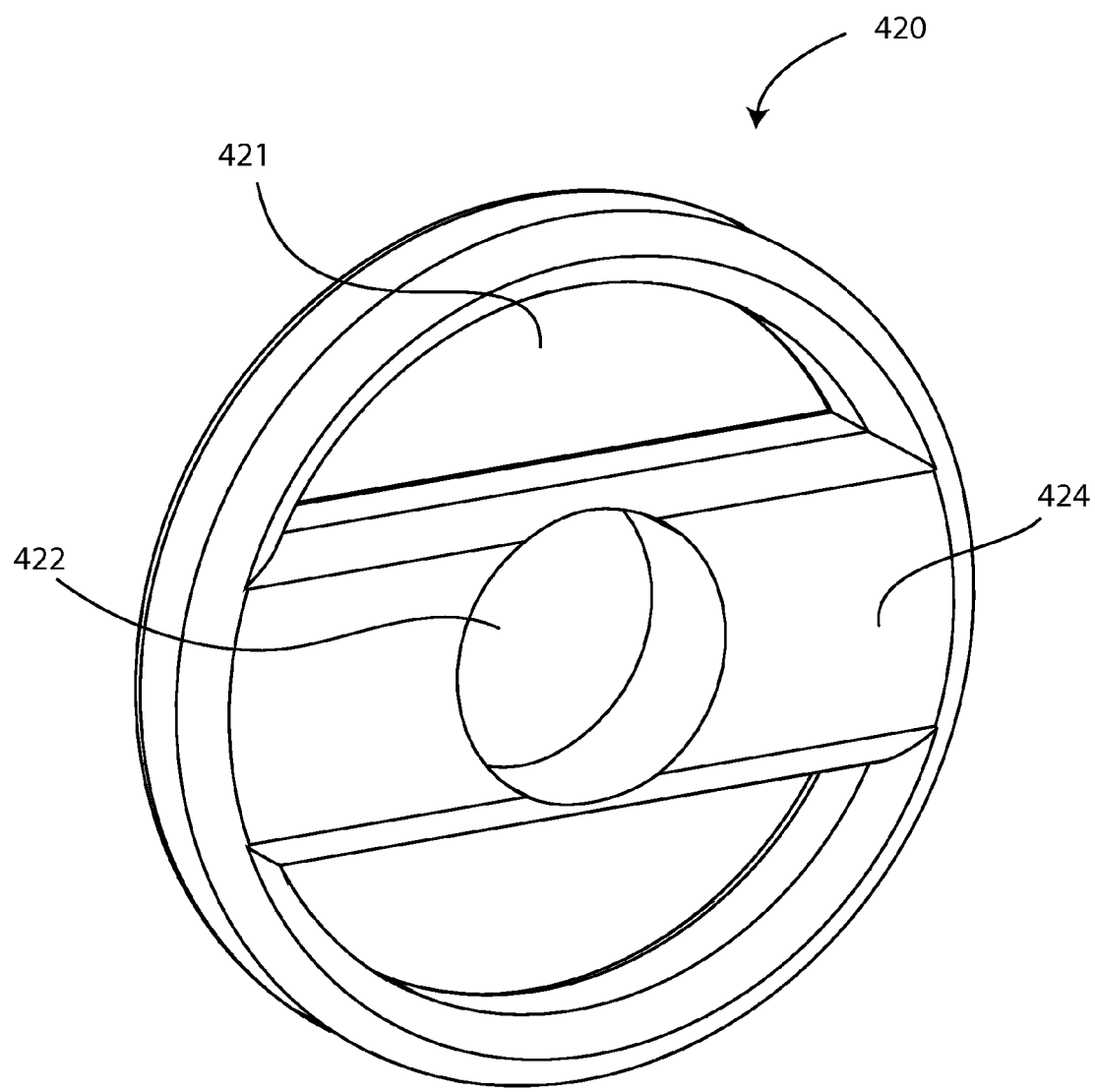
FIG. 12B is a top view of yet another fixation device.
Figure 12C:
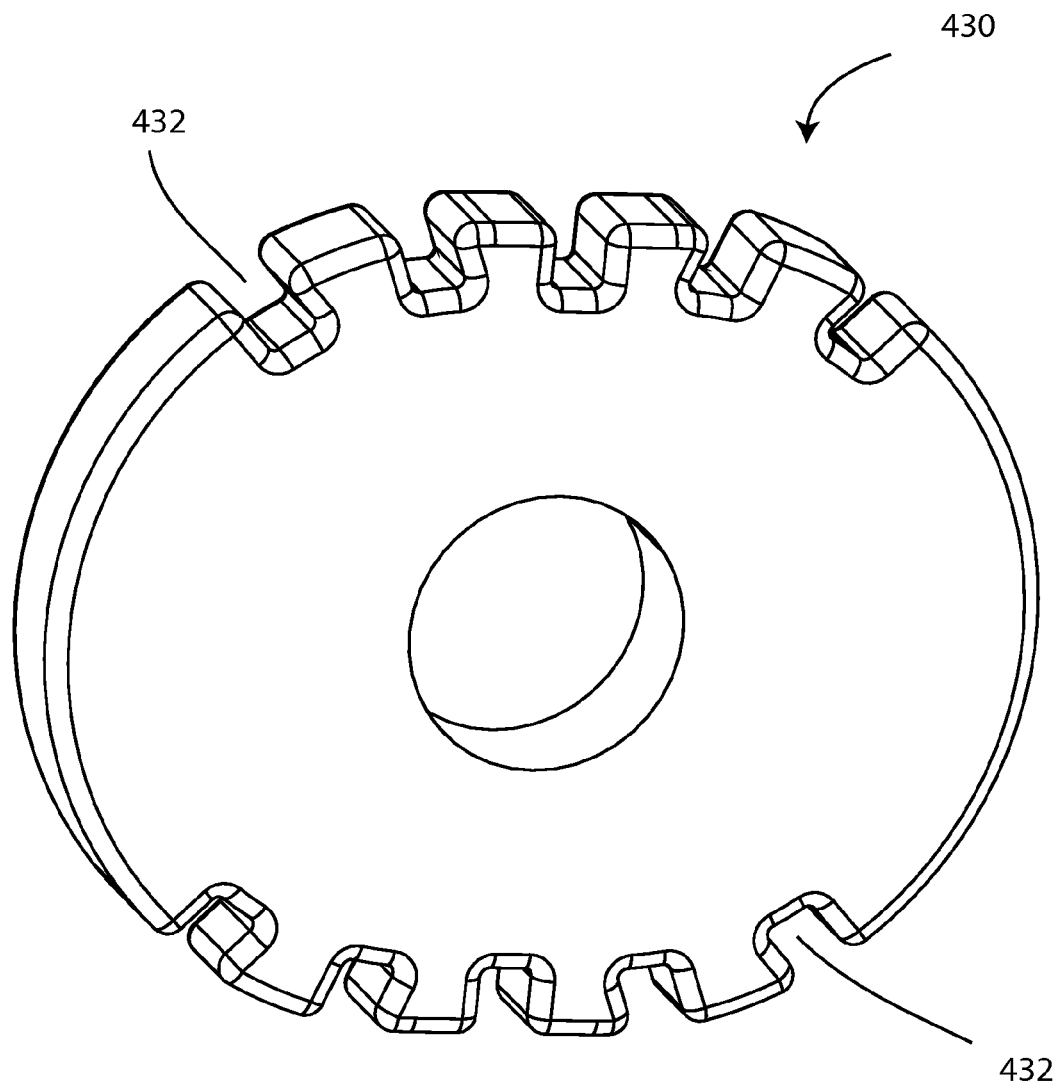
FIG. 12C is a top view of yet another fixation device.

Referring to FIGS. 12A-12C, washers 410, 420, and 430 are shown, respectively. Washer 410 forms a portion of a full circle or oval, and includes peripheral notches 412 around the circular portion. This may increase visibility and flexibility in surgical uses. Washer 420 forms a full circle, and includes a large central aperture 421 which is spanned by a bar 424. This may increase visibility of the graft and/or sutures. The bar 424 can also have an aperture 422 formed therein and configured to receive a screw construct (not shown). Washer 430 is circular or oval, and includes peripheral notches 432. This may increase flexibility in surgical uses. Washers 410, 420, and 430 may be used in place of other washers disclosed herein. Any of the washers disclosed herein may include features to permit adjustment and locking of a line, such as a suture, to the washer, such as nothches or grooves. In other examples (not shown), the washers can have one or more narrowing slits around the periphery of the washer. The narrowing slits can be open wider toward the outer periphery of the washer and narrow toward the inner portion of the washer. In this manner, the suture can be easily guided into the narrowing slit. The narrowing slits can also have a final width toward the inner portion of the washer that is less than or equal to the width of the suture, such that the suture becomes "wedged" or trapped in the narrowing slit and held in place by the narrowing slit. Any of the washers disclosed herein can have one or more narrowing slits around the periphery of the washer in place of, or in addition to the other features disclosed herein.

Figure 13:
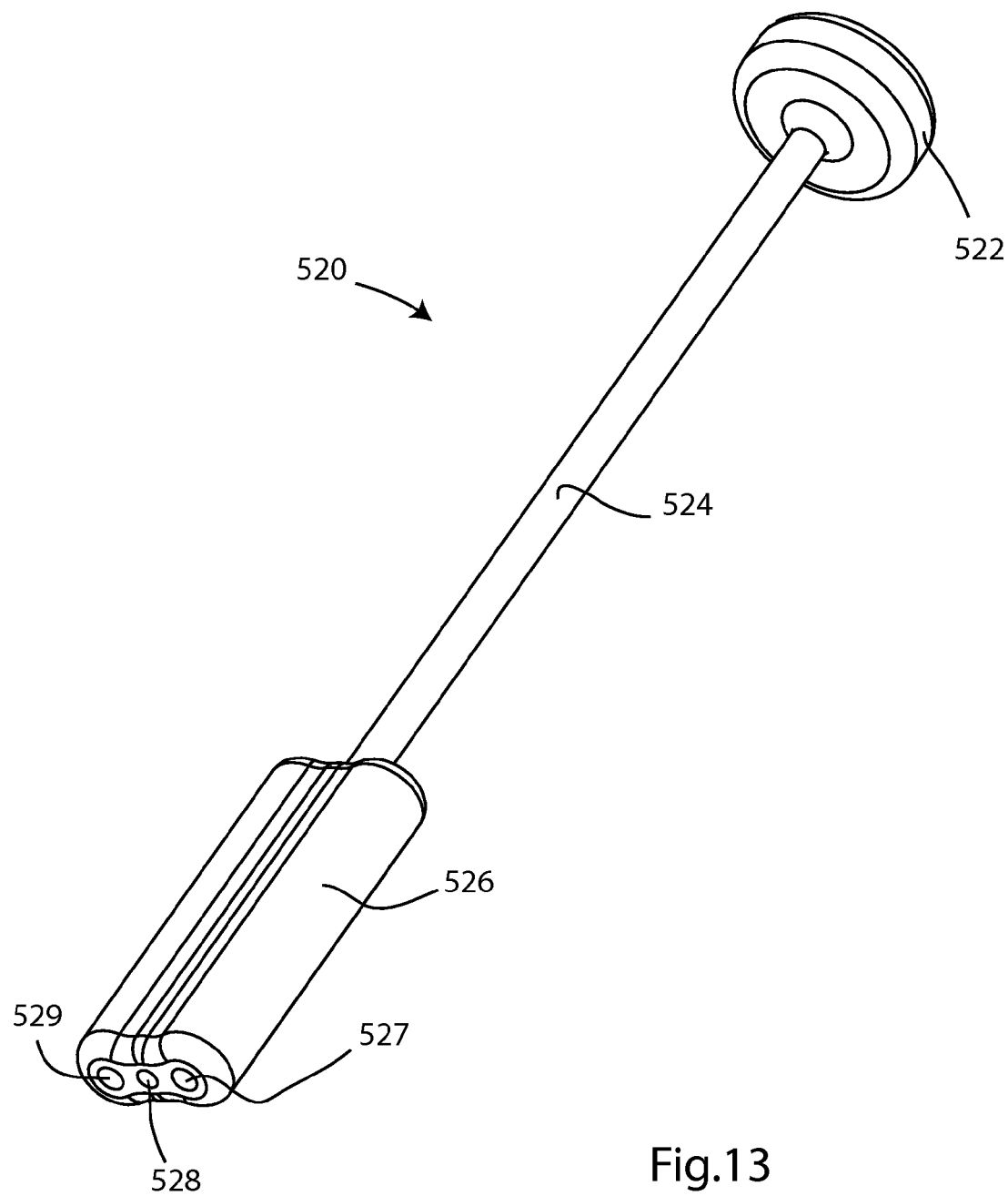
FIG. 13 is a perspective view of a tamp tool.

Referring to FIG. 13, an example of a bone tamp 520 for shaping a bone tunnel is shown. The tamp 520 can be cannulated and configured to receive a guide wire (not shown) to guide the tamp 520 to the bone tunnel. The guide wire can be fed through aperture or cannulation 528. The tamp 520 may include a handle 522, a shaft 524, and a body 526. The handle 522 may include a striking platform. In the example shown, additional cannulations 527, 529 are included. The body 526 may have a cross-sectional shape that is oblong, bowtie shaped, figure eight shaped, dumbbell shaped, bicuspid epicycloid shaped, or Gerono lemniscate shaped. A cross-sectional area of the body 526, transverse to the longitudinal axis of the shaft 524, can have a plurality of lobes (not shown) having a height and a width, wherein the height of the lobes is greater than the width of the lobes. The cross-sectional area of the body 526 transverse to the longitudinal axis can have a figure eight shape (not shown) with two lobes overlapping each other forming a pair of indentations (not shown). The pair of indentations can have at least one concave portion and at least one convex portion. The body 526 can also include cutting surfaces (not shown) which protrude from the sides of the body 526 and configured to remove pieces of bone as the body 526 is advanced into the bone tunnel. The body 526 can also have at least one recessed area (not shown) adjacent to the at least one cutting surface and configured to capture the removed portions of bone as the tool is advanced into the bone tunnel. The body 526 can also have at least one aperture configured to facilitate removal of trapped bone portions. In use, the guide wire may be positioned in the bone relative to the bone tunnel. The guide wire may be received in cannulation 528 so that the body 526 slides into the bone tunnel along the guide wire. The tamp 520 may be pushed or impacted into the tunnel to refine the size and/or shape of the tunnel to receive an implant. In another example of use, the guide wire may be received in one of the additional cannulations 527, 529 to offset the tamp 520 relative to the bone tunnel. In this example, the tamp 520 may asymmetrically refine the size and/or shape of the tunnel.

Figure 14:
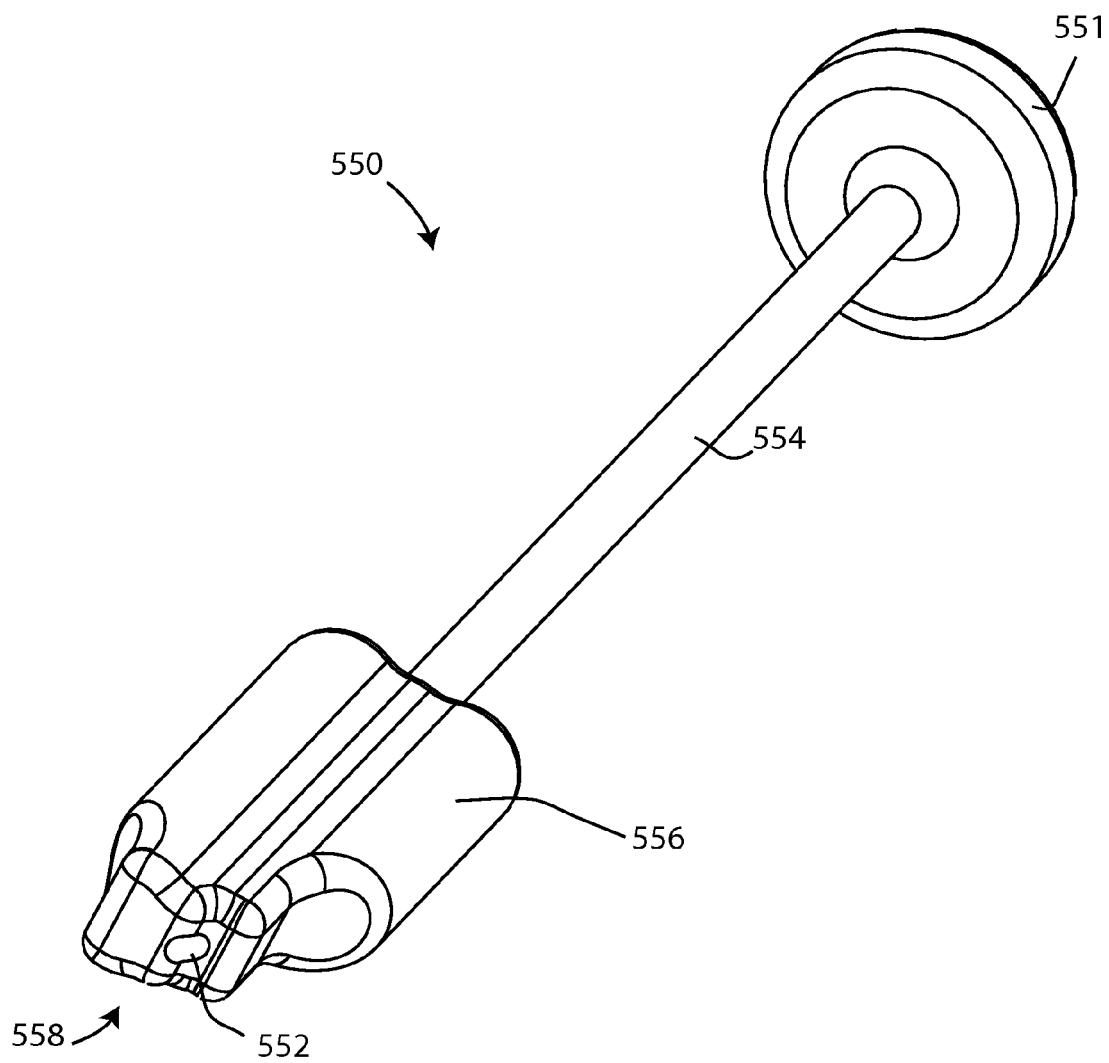
FIG. 14 is a perspective view of another tamp tool.

Referring to FIG. 14, another example of a tamp 550 is shown. The tamp 550 may share some or all of the characteristics of the tamp 520. The tamp 550 may include a handle or impact member 551, a shaft 554 and a body 556. The handle 522 may include a striking platform. The body 556 may have a cross-sectional shape that is oblong, bowtie shaped, figure eight shaped, dumbbell shaped, bicuspid epicycloid shaped, or Gerono lemniscate shaped. The tamp 550 can be cannulated 552 and configured to receive a guide wire (not shown) to guide the tamp 550 to the bone tunnel. A leading portion 558 of the body 556 may be reduced in size and/or may be shaped to fit an unmodified bone tunnel. The leading portion 558 may also be described as a guide tip. In use, the leading portion 558 may be easily introduced into the bone tunnel. The tamp 550 may then be pushed or impacted to drive it further into the tunnel. The leading portion 558 may follow the bone tunnel to guide the tamp 550 along the tunnel.

The preceding disclosure contemplates a single bone tunnel with a non-circular cross section. More specifically, the preceding disclosure contemplates a tunnel whose cross section is shaped like an oblong, a bowtie, a figure eight, a dumbbell, a bicuspid epicycloid, or a Gerono lemniscate, or another shape which has a length greater than its width and a narrowing or constricted midportion across its width. Other bone tunnels are also contemplated. For example, two separate bone tunnels are contemplated. The bone tunnels can be formed in the tibia, for example. The tunnels may be parallel, intersecting, or skewed. Parallel or skewed tunnels may be separated by a bone bridge. Separate tibial tunnels may facilitate independent tensioning of the AM and PL graft bundles at relevant knee flexion angles.

Figure 15:
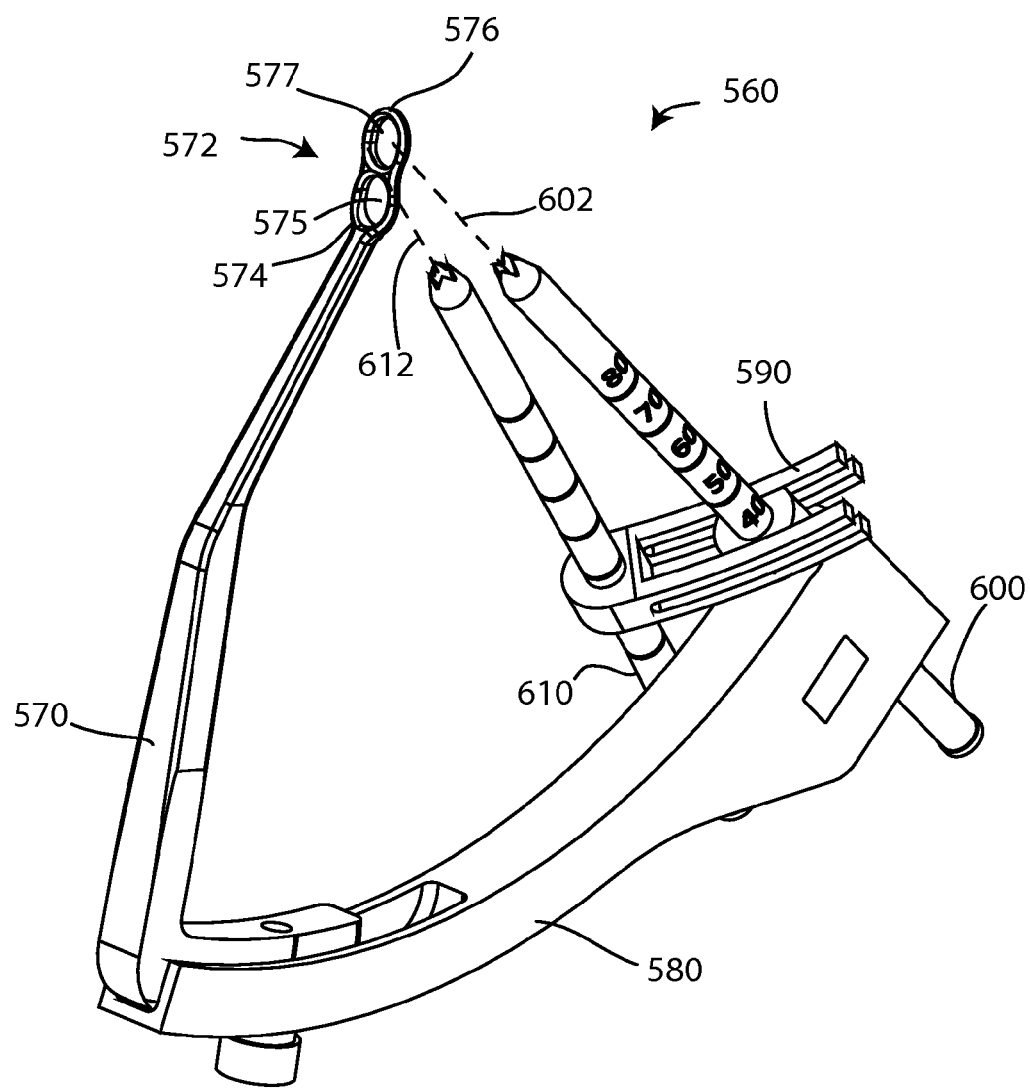
FIG. 15 is a perspective view of a double drill guide.

Referring to FIG. 15, an example of a tibial drill guide 560 is shown. The drill guide 560 may include an arm 570, a first rail 580, a second rail 590, a first guide tube 600, and a second guide tube 610. The arm 570 may include a working portion 572, which may include a first loop 574 which is pierced by an aperture 575. The working portion 572 may also include a second loop 576 pierced by a second aperture 577, adjacent to the first loop 574. The working portion 572 may be pressed against the tibial ACL attachment area so that the first loop 574 is centered in the antero-medial bundle attachment area and the second loop 576 is generally centered in the postero-lateral bundle attachment area. Alternatively, the entire working portion 572 may be generally aligned with and centered in the total tibial ACL attachment area. The working portion 572 may include a grip member, such as a spike or tooth (not shown) to dig into the tibial plateau. The first rail 580 may be arcuate. The first guide tube 600 may be carried on the first rail 580 so that a center longitudinal axis 602 of the guide tube always passes through a center point of the aperture 575, regardless of the position of the first guide tube along the first rail. The second rail 590 may also be arcuate. The second guide tube 610 may be carried on the second rail 590 so that a center longitudinal axis 612 of the guide tube always passes through a center point of the aperture 577, regardless of the position of the second guide tube along the second rail. The second rail 590 may be held at an angle with respect to the first rail 580. The angle may be fixed or variable. For example, the first and second rails 580, 590 may be formed as a single part or rigidly fixed together. In another example, the first and second rails 580, 590 may be hinged together near the arm 570. The second guide tube 610 may be held at an angle with respect to the first guide tube 600. The angle may be fixed or variable. For example, the first and second guide tubes 600, 610 may move together along the rails 580, 590 in a fixed relationship. In another example, the first and second guide tubes 600, 610 may each be independently movable along the rails 580, 590. The tibial drill guide 560 may include means to ensure that the axis 602 always passes through the center of the aperture 575 and the axis 612 always passes through the center of the aperture 577, regardless of the magnitude of the angle.

Any of the fixation devices disclosed herein may be adapted for use in the femur, the tibia, or in other suspensory fixation applications, as mentioned previously.

Any of the devices described herein may be fabricated from metals, alloys, polymers, plastics, ceramics, glasses, composite materials, or combinations thereof. Different materials may be used within a single part.

Those skilled in the art will appreciate that various adaptations and modifications of the just described preferred embodiments can be configured without departing from the scope and spirit of the invention. Therefore, it is to be understood that, within the scope of the above description, the invention may be practiced other than as specifically described herein.

It should be understood that the present apparatuses and methods are not intended to be limited to the particular forms disclosed. Rather, they are intended to include all modifications, equivalents, and alternatives falling within the scope of the claims. They are further intended to include embodiments which may be formed by combining features from the disclosed embodiments, and variants thereof.

The claims are not to be interpreted as including means-plus-function or step-plus-function limitations, unless such a limitation is explicitly recited in a given claim using the phrase(s) "means for" or "step for," respectively.

The term "coupled" is defined as connected, although not necessarily directly, and not necessarily mechanically.

The use of the word "a" or "an" when used in conjunction with the term "comprising" in the claims and/or the specification may mean "one," but it is also consistent with the meaning of "one or more" or "at least one." The term "about" means, in general, the stated value plus or minus 5%. The use of the term "or" in the claims is used to mean "and/or" unless explicitly indicated to refer to alternatives only or the alternative are mutually exclusive, although the disclosure supports a definition that refers to only alternatives and "and/or."

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements, possesses those one or more steps or elements, but is not limited to possessing only those one or more elements. Likewise, a step of a method or an element of a device that "comprises," "has," "includes" or "contains" one or more features, possesses those one or more features, but is not limited to possessing only those one or more features. Furthermore, a device or structure that is configured in a certain way is configured in at least that way, but may also be configured in ways that are not listed.

The present invention may be embodied in other specific forms without departing from its spirit or essential characteristics. It is appreciated that various features of the above-described examples can be mixed and matched to form a variety of other alternatives. As such, the described embodiments are to be considered in all respects only as illustrative and not restrictive. Similarly, manufacturing, assembly methods, and materials described for one device may be used in the manufacture or assembly of another device. The scope of the invention is, therefore, indicated by the appended claims rather than by the foregoing description. All changes which come within the meaning and range of equivalency of the claims are to be embraced within their scope.

The invention claimed is:

1. A tool for implanting a ligament graft in a patient comprising: a handle portion; an elongate member comprising: a proximal end engaged with the handle portion; and a distal end; and at least one attachment member; wherein the at least one attachment member is proximal the distal end of the elongate member, the at least one attachment member is configured to engage a first portion of at least one ligament graft, the distal end of the elongate member is configured to engage a second portion of the at least one ligament graft, wherein a tension force is applied to the at least one ligament graft between the first portion of the at least one ligament graft engaged with the at least one attachment member and the second portion of the at least one ligament graft engaged with the distal end of the elongate member, wherein the elongate member is translatable in the proximal to distal direction to selectively increase and decrease the tension force applied to the at least one ligament graft; a tension member configured to impart a user selectable tension force to the at least one ligament graft within a predetermined range of tension forces, wherein the tension member is a spring, wherein the predetermined range of tension forces is between about zero pounds of tension force and about twenty two pounds of tension force; and a knob configured to rotate in a first direction to increase the tension force applied to the at least one ligament graft and rotate in a second direction to decrease the tension force applied to the at least one ligament graft.

2. The tool of claim 1, further comprising a plunger engaged with the elongate member, the plunger configured to translate in a first direction to increase the tension force applied to the at least one ligament graft and translate in a second direction to decrease the tension force applied to the at least one ligament graft.

3. The tool of claim 2, further comprising a ratcheting mechanism between the plunger and the handle portion, the ratcheting mechanism configured to allow the plunger to translate in the first direction and prevent the plunger from translating in the second direction to allow the user to select and maintain a tension force applied to the at least one ligament graft.

4. The tool of claim 3, further comprising a ratchet release mechanism configured to selectively disengage the ratcheting mechanism and allow the plunger to translate in the second direction.

5. The tool of claim 1, wherein the elongate member further comprises an inner shaft and an outer shaft, wherein the proximal end of the inner shaft is engaged with the distal end of the spring and the proximal end of the outer shaft is engaged with the proximal end of the spring.

6. The tool of claim 5, wherein the inner shaft further comprises a distal stop member, configured to interact with the distal end of the outer shaft to apply a tension force greater than the predetermined range of forces.

7. The tool of claim 5, further comprising a holding member configured to prevent accidental removal of the inner or outer shafts from the handle portion, and prevent rotational movement of the inner or outer shafts with respect to the handle portion.

8. The tool of claim 1, wherein the distal end of the elongate member further comprises a fixation device attachment feature adapted to receive a fixation device.

9. The tool of claim 8, wherein the fixation device attachment feature comprises a protrusion configured to be at least partially inserted into the fixation device.

10. The tool of claim 8, wherein the fixation device attachment feature comprises threading configured to interact with complimentary shaped threading formed in the fixation device.

11. The tool of claim 8, wherein the elongate member has a longitudinal axis and the cross-sectional area of the elongate member is less than the cross-sectional area of the fixation device attached to the elongate member with the cross-sectional areas taken transverse to the longitudinal axis.

12. The tool of claim 1, wherein the distal end of the elongate member further comprises a groove for receiving the second portion of the at least one ligament graft.

13. The tool of claim 1, wherein the at least one attachment member is engaged with the handle portion.

14. The tool of claim 13, wherein the at least one attachment member further comprises at least one ligament graft attachment feature.

15. The tool of claim 14, wherein the at least one ligament graft attachment feature comprises a slit configured to receive a suture that is engaged with the at least one ligament graft.

16. The tool of claim 1, wherein the at least one attachment member is translatable in the proximal to distal direction to selectively apply and release the tension force applied to the at least one ligament graft.

17. A tool for implanting a ligament graft in a patient comprising: a handle portion; an elongate member comprising: a proximal end engaged with the handle portion; and a distal end, distal from the handle portion; a first attachment member engaged with the handle portion on a first side of the handle portion; and a second attachment member engaged with the handle portion on a second side of the handle portion; wherein the first attachment member is configured to engage a first portion of at least one ligament graft, the second attachment member is configured to engage a second portion of the at least one ligament graft, and the distal end of the elongate member is configured to engage a third portion of the at least one ligament graft, the third portion of the at least one ligament graft intermediate the first and second portions of the at least one ligament graft; wherein a first tension force is applied to the at least one ligament graft between the first and third portions of at least one ligament graft, and wherein a second tension force is applied to the at least one ligament graft between the second and third portions of at least one ligament graft, wherein the elongate member is translatable in the proximal to distal direction to selectively apply and release the tension force applied to the at least one ligament graft; a tension member configured to impart a user selectable tension force to the at least one ligament graft within a predetermined range of tension forces, wherein the tension member is a spring, wherein the predetermined range of tension forces is between about zero pounds of tension force and about twenty two pounds of tension force; and a knob configured to rotate in a first direction to increase the tension force applied to the at least one ligament graft and rotate in a second direction to decrease the tension force applied to the at least one ligament graft.

18. The tool of claim 17, wherein the elongate member further comprises an inner shaft and an outer shaft, wherein the proximal end of the inner shaft is engaged with the distal end of the spring and the proximal end of the outer shaft is engaged with the proximal end of the spring.

19. The tool of claim 18, wherein the inner shaft further comprises a distal stop member, configured to interact with the distal end of the outer shaft to apply a tension force greater than the predetermined range of forces.

20. The tool of claim 18, further comprising a holding member configured to prevent accidental removal of the inner or outer shafts from the handle portion and prevent rotational movement of the inner or outer shafts with respect to the handle portion.

21. The tool of claim 17, wherein the distal end of the elongate member further comprises a fixation device attachment feature adapted to receive a fixation device.

22. The tool of claim 21, wherein the fixation device attachment feature comprises a protrusion configured to be at least partially inserted into the fixation device.

23. The tool of claim 21, wherein the elongate member has a longitudinal axis and the cross-sectional area of the elongate member is less than the cross-sectional area of the fixation device attached to the elongate member with the cross-sectional areas taken transverse to the longitudinal axis.

24. The tool of claim 17, wherein the first attachment member comprises two ligament graft attachment features and the second attachment member comprises two ligament graft attachment features.

25. The tool of claim 24, wherein the two ligament graft attachment features of the first attachment member and the two ligament graft attachment features of the second attachment member comprise slits configured to receive sutures engaged with the at least one ligament graft.

* * * * *